US 6,554,991 B1

(12) United States Patent
Goodman et al.

(10) Patent No.: US 6,554,991 B1
(45) Date of Patent: Apr. 29, 2003

(54) AUTOMATED SYSTEM FOR TWO-DIMENSIONAL ELECTROPHORESIS

(75) Inventors: Jack Goodman, Lusby, MD (US); N. Leigh Anderson, Washington, DC (US)

(73) Assignee: Large Scale Proteomics Corporation, Germantown, MD (US)

( * ) Notice: Subject to any disclaimer, the term of this patent is extended or adjusted under 35 U.S.C. 154(b) by 210 days.

(21) Appl. No.: 09/667,567

(22) Filed: Sep. 21, 2000

Related U.S. Application Data

(60) Continuation-in-part of application No. 09/339,164, filed on Jun. 24, 1999, now Pat. No. 6,245,206, which is a division of application No. 08/881,761, filed on Jun. 24, 1997, now Pat. No. 5,993,627.

(51) Int. Cl.[7] .................. G01N 27/447; G01N 1/00; C12M 3/00
(52) U.S. Cl. .................. 204/613; 435/287.3; 73/863
(58) Field of Search .................. 204/462, 613, 204/466, 616; 435/287.3, 287.1; 73/863, 863.31, 863.32

(56) References Cited

U.S. PATENT DOCUMENTS

| | | | |
|---|---|---|---|
| 3,499,360 A | 3/1970 | Davis | |
| 3,526,480 A | 9/1970 | Findl et al. | |
| 3,766,047 A | 10/1973 | Elevitch | |
| 3,767,560 A | 10/1973 | Elevitch | |
| 3,839,183 A | 10/1974 | Klein et al. | |
| 4,088,561 A | 5/1978 | Anderson | |
| 4,130,470 A | 12/1978 | Rosengren et al. | |
| 4,169,036 A | 9/1979 | Anderson et al. | |
| 4,221,533 A | 9/1980 | Heim et al. | |
| 4,341,735 A | 7/1982 | Seifried | |
| 4,375,401 A | 3/1983 | Catsimpoolas | |
| 4,391,689 A | 7/1983 | Golias | |
| 4,440,500 A * | 4/1984 | Schneider | 366/162.5 |
| 4,460,525 A | 7/1984 | Ansorge | |
| 4,592,089 A | 5/1986 | Hartman | |
| 4,684,613 A | 8/1987 | Barrere et al. | |
| 4,704,198 A | 11/1987 | Ebersole et al. | |
| 4,764,815 A * | 8/1988 | Landsman | 358/496 |
| 4,812,392 A | 3/1989 | Miyake et al. | |
| 4,886,643 A * | 12/1989 | Feist | 422/133 |
| 4,892,639 A | 1/1990 | Sarrine et al. | |
| 4,909,920 A | 3/1990 | Sarrine et al. | |
| 4,920,422 A * | 4/1990 | Lapierre | 358/296 |
| 4,944,483 A | 7/1990 | Nishizawa | |
| 4,954,237 A | 9/1990 | Sarrine et al. | |
| 5,020,693 A * | 6/1991 | Ernst et al. | 222/137 |
| 5,021,046 A * | 6/1991 | Wallace | 604/97.3 |
| 5,045,164 A | 9/1991 | Tansamrit et al. | |
| 5,066,276 A * | 11/1991 | Wang | 604/521 |
| 5,073,863 A | 12/1991 | Zhang | |
| 5,074,981 A | 12/1991 | Fairfield | |

(List continued on next page.)

FOREIGN PATENT DOCUMENTS

| | | |
|---|---|---|
| EP | 0 539 888 A1 | 5/1993 |
| GB | 9624927.1 | 11/1996 |
| WO | WO 98/23950 | 6/1998 |
| WO | WO 98/47006 | 10/1998 |
| WO | WO 99/15875 | 4/1999 |
| WO | 0049397 * | 8/2000 |
| WO | WO 00/57153 | 9/2000 |

Primary Examiner—T. Tung
Assistant Examiner—Alex Noguerola
(74) Attorney, Agent, or Firm—Rothwell, Figg, Ernst & Manbeck, p.c.

(57) ABSTRACT

The present invention provides an integrated, fully automated, high-throughput system for two-dimensional electrophoresis comprised of gel-making machines, gel processing machines, gel compositions and geometries, gel handling systems, sample preparation systems, software and methods. The system is capable of continuous operation at high-throughput to allow construction of large quantitative data sets.

41 Claims, 25 Drawing Sheets

U.S. PATENT DOCUMENTS

| | | |
|---|---|---|
| 5,098,539 A | 3/1992 | Shieh |
| 5,164,065 A | 11/1992 | Bettencourt et al. |
| 5,164,066 A | 11/1992 | Yetman et al. |
| 5,217,591 A | 6/1993 | Gombocz et al. |
| 5,275,710 A | 1/1994 | Gombocz et al. |
| 5,304,292 A | 4/1994 | Jacobs et al. |
| 5,348,883 A | 9/1994 | Togawa |
| 5,434,049 A | 7/1995 | Okano et al. ................ 435/6 |
| 5,447,612 A | 9/1995 | Bier et al. |
| 5,449,446 A | 9/1995 | Verma et al. |
| 5,507,934 A | 4/1996 | Renfrew |
| 5,520,790 A | 5/1996 | Chopas et al. |
| 5,535,021 A * | 7/1996 | Chiang et al. ............... 358/474 |
| 5,540,498 A | 7/1996 | Chu |
| 5,583,279 A * | 12/1996 | Sarrine et al. ............... 73/1.02 |
| 5,587,062 A | 12/1996 | Togawa et al. |
| 5,589,104 A | 12/1996 | Bambeck |
| 5,717,602 A | 2/1998 | Kenning |
| 5,753,095 A | 5/1998 | Alpenfels et al. |
| 5,777,660 A * | 7/1998 | Ard ............................ 347/260 |
| 5,949,899 A | 9/1999 | Ng |
| 6,064,754 A | 5/2000 | Parekh et al. |
| 6,278,794 B1 | 8/2001 | Parekh et al. ............... 382/129 |

\* cited by examiner

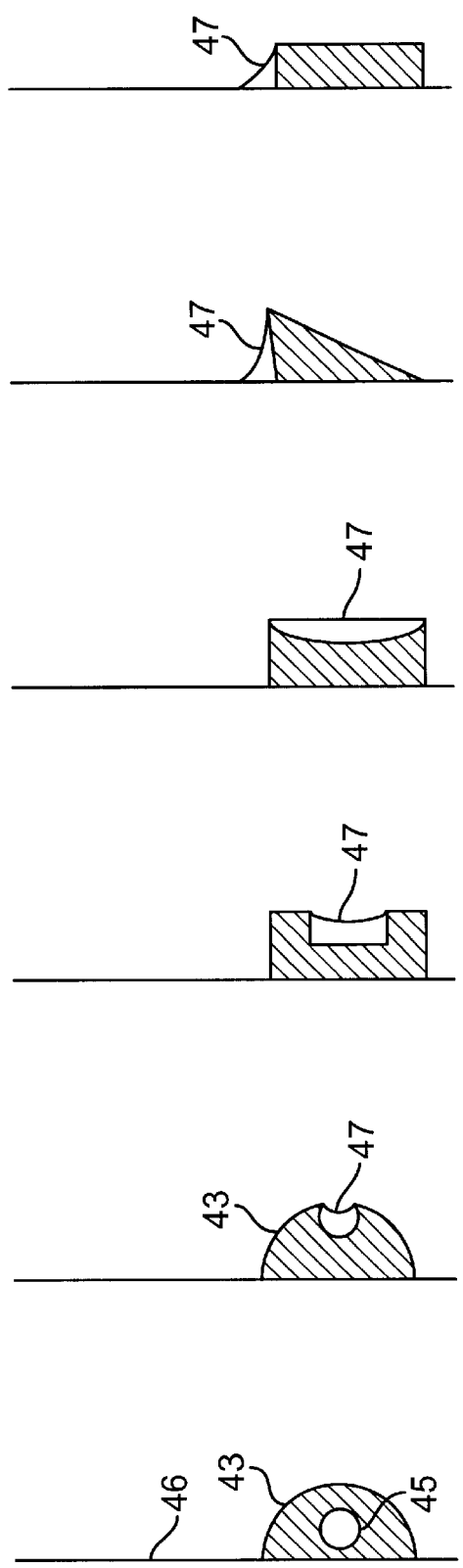

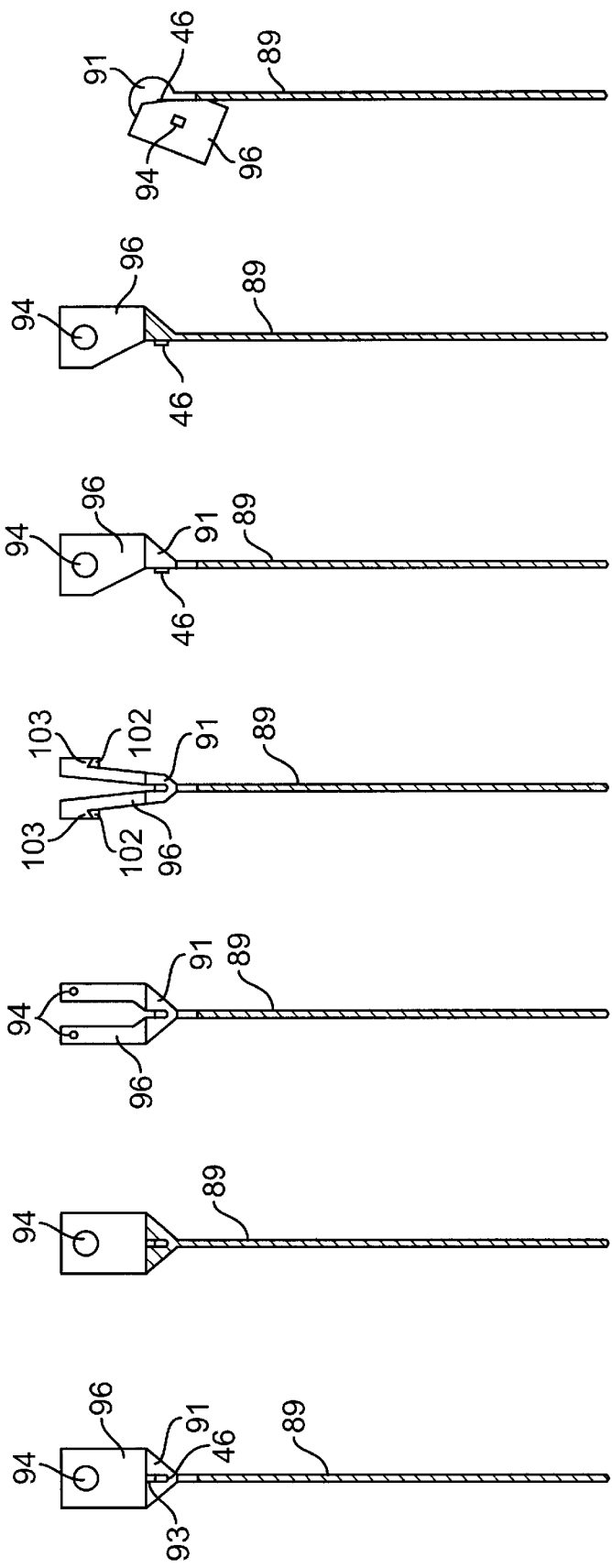

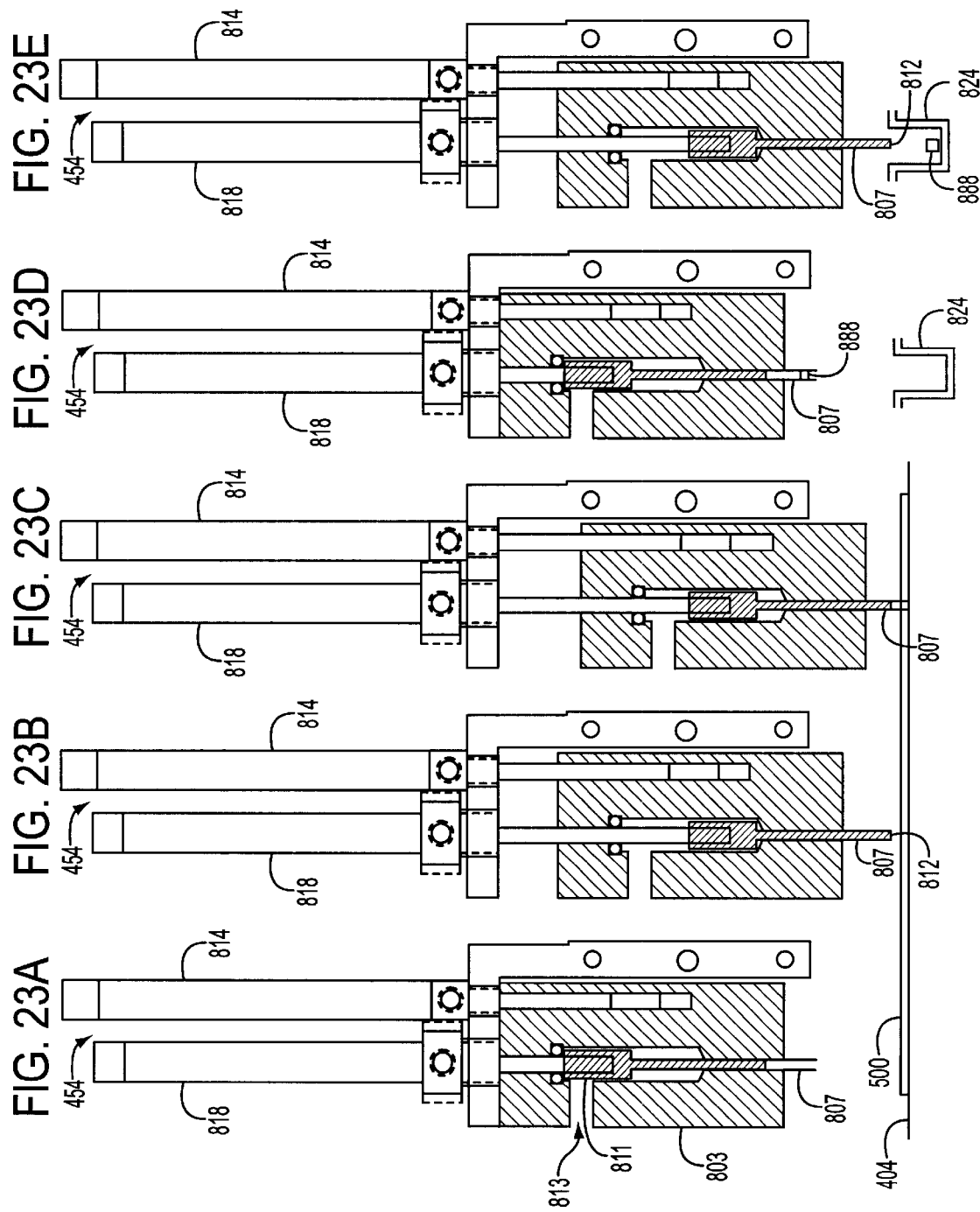

AUTOMATED SYSTEM FOR TWO-DIMENSIONAL ELECTROPHORESIS

CROSS-REFERENCE TO RELATED APPLICATION

The present application is a continuation-in-part of U.S. patent application Ser. No. 09/339,164, filed Jun. 24, 1999, now U.S. Pat. No. 6,245,206, which was a division of U.S. patent application Ser. No. 08/881,761, filed Jun. 24, 1997, that issued Nov. 30, 1999 as U.S. Pat. No. 5,993,627. +gi

STATEMENT REGARDING FEDERALLY SPONSORED RESEARCH OR DEVELOPMENT

This invention was made with United States Government support under cooperative agreement number 70NANB5H1075 awarded by the National Institute of Standards and Technology.

BACKGROUND OF THE INVENTION

The invention relates to the field of electrophoretic separations of macromolecules and in particular, to the automation of two-dimensional electrophoretic separations used in the analysis of proteins. Such two-dimensional procedures typically involve sequential separations by isoelectric focusing (IEF) and SDS slab gel electrophoresis, and an automated 2-D method thus involves manufacture and use of gel media for both isoelectric focusing and SDS electrophoresis, together with means for protein detection and quantitation. Two-dimensional electrophoresis technology forms the basis of the expanding field of proteomics, and hence automation of the procedure is a critical requirement for scale-up of efforts to build proteome databases comprising all the proteins of complex organisms such as man. To date no successful automation efforts have been reported, despite the use of bench-scale 2-D electrophoresis in more than 5,000 scientific publications.

The publications and other materials used herein to illuminate the background of the invention and in particular, cases to provide additional details respecting the practice, are incorporated herein by reference, and for convenience are referenced in the following text and respectively grouped in the appended List of References. Elements of the invention are disclosed in our Disclosure Documents 393753, 393754 and 412899.

Isoelectric Focusing (IEF)

A protein is a macromolecule composed of a chain of amino acids. Of the 20 amino acids found in typical proteins, four (aspartic and glutamic acids, cysteine and tyrosine) carry a negative charge and three (lysine, arginine and histidine) a positive charge, in some pH range. A specific protein, defined by its specific sequence of amino acids, is thus likely to incorporate a number of charged groups along its length. The magnitude of the charge contributed by each amino acid is governed by the prevailing pH of the surrounding solution, and can vary from a minimum of 0 to a maximum of 1 charge (positive or negative depending on the amino acid), according to a titration curve relating charge and pH according to the pK of the amino acid in question. Under denaturing conditions in which all of the amino acids are exposed, the total charge of the protein molecule is given approximately by the sum of the charges of its component amino acids, all at the prevailing solution pH.

Two proteins having different ratios of charged, or titrating, amino acids can be separated by virtue of their different net charges at some pH. Under the influence of an applied electric field, a more highly charged protein will move faster than a less highly charged protein of similar size and shape. If the proteins are made to move from a sample zone through a non-convecting medium (typically a gel such as polyacrylamide), an electrophoretic separation will result.

If, in the course of migrating under an applied electric field, a protein enters a region whose pH has that value at which the protein's net charge is zero (the isoelectric pH), it will cease to migrate relative to the medium. Further, if the migration occurs through a monotonic pH gradient, the protein will "focus" at this isoelectric pH value. If it moves toward more acidic pH values, the protein will become more positively charged, and a properly-oriented electric field will propel the protein back towards the isoelectric point. Likewise, if the protein moves towards more basic pH values, it will become more negatively charged, and the same field will push it back toward the isoelectric point. This separation process, called isoelectric focusing, can resolve two proteins differing by less than a single charged amino acid among hundreds in the respective sequences.

A key requirement for an isoelectric focusing procedure is the formation of an appropriate spatial pH gradient. This can be achieved either dynamically, by including a heterogeneous mixture of charged molecules (ampholytes) into an initially homogeneous separation medium, or statically, by incorporating a spatial gradient of titrating groups into the gel matrix through which the migration will occur. The former represents classical ampholyte-based isoelectric focusing, and the latter the more recently developed immobilized pH gradient (IPG) isoelectric focusing technique. The IPG approach has the advantage that the pH gradient is fixed in the gel, while the ampholyte-based approach is susceptible to positional drift as the ampholyte molecules move in the applied electric field. The best current methodology combines the two approaches to provide a system where the pH gradient is spatially fixed but small amounts of ampholytes are present to decrease the adsorption of proteins onto the charged gel matrix of the IPG.

It is current practice to create IPG gels in a thin planar configuration bonded to an inert substrate, typically a sheet of Mylar plastic which has been treated so as to chemically bond to an acrylamide gel (e.g., Gelbond® PAG film, FMC Corporation). The IPG gel is typically formed as a rectangular plate 0.5 mm thick, 10 to 30 cm long (in the direction of separation) and about 10 cm wide. Multiple samples can be applied to such a gel in parallel lanes, with the attendant problem of diffusion of proteins between lanes producing cross contamination. In the case where it is important that all applied protein in a given lane is recovered in that lane (as is typically the case in 2-D electrophoresis), it has proven necessary to split the gel into narrow strips (typically 3 mm wide), each of which can then be run as a separate gel. Since the protein of a sample is then confined to the volume of the gel represented by the single strip, it will all be recovered in that strip. Such strips (Immobiline DryStrips) are produced commercially by Pharmacia Biotech.

While the narrow strip format solves the problem of containing samples within a recoverable, non-cross-contaminating region, there remain substantial problems associated with the introduction of sample proteins into the gel. Since protein-containing samples are typically prepared in a liquid form, the proteins they contain must migrate, under the influence of the electric field, from a liquid-holding region into the IPG gel in order to undergo separation. This is typically achieved by lightly pressing an open-bottomed rectangular frame against the planar gel surface so that the gel forms the bottom of an open-topped but otherwise liquid-tight vessel (the sample well). The sample is then deposited in this well in contact with the gel surface forming the bottom of the well. Since all of the sample protein must pass through a small area on the surface of the gel (the well bottom) in order to reach the gel interior, the local concentration of protein at the entry point can become very high, leading to protein precipitation. The sample entry area is typically smaller than the gel surface forming the well bottom because the protein migrates into the gel under the influence of an electric field which directs most of it to one edge of the well bottom, tending to produce protein precipitation. The major source of precipitation, however, is provided by the charged groups introduced into the gel matrix to form the pH gradient in IPG gels: these groups can interact with charges on the proteins (most of which are not at their isoelectric points at the position of the application point and hence have non-zero net charges) to bind precipitates to the gel. It is common experience that separations of the same protein mixture on a series of apparently identical IPG gels can yield very different quantitative recoveries of different proteins at their respective isoelectric points, indicating that the precipitation phenomenon may vary from gel to gel in unpredictable ways, thereby frustrating the general use of IPG gels for quantitative protein separations.

Recently, methods have been introduced in which the IPG strip is re-swollen, from the dry state, in a solution containing sample proteins, with the intention that the sample proteins completely permeate the gel at the start of the run.

Isoelectric focusing separation of proteins in an immobilized pH gradient (IPG) is extensively described in the art. The concept of the IPG is disclosed in U.S. Pat. No. 4,130,470 and is further described in numerous publications. The IPG gel strips manufactured are generally of simple planar shape.

A series of disclosures have dealt with various configurations of cavities ("sample wells") used for the application of macromolecular-containing samples to the surfaces of gels, most frequently slab gels used for protein or nucleic acid separations. In each case, these sample wells were designed to concentrate macromolecules in the sample into a thin starting zone prior to their migration through the resolving gel. The following references describe the use of devices placed against a gel to form wells: U.S. Pat. No. 5,304,292 describes the use of pieces of compressible gasket to form well walls at the top of a slab where the ends of the pieces touch the top edge of the slab. U.S. Pat. No. 5,164,065 describes a shark's tooth comb used in combination with DNA sequencing gels.

Several references describe automated devices for creating gradients of polymerizable monomers. Such systems have been used for making porosity gradient gels used in molecular weight separations of proteins. Altland et al. (Altland, K. and Altland, A. Pouring reproducible gradients in gels under computer control, *Clin.Chem.* 30(12 Pt 1):2098–2103, 1984) shows the use of such systems for creating the gradients of titratable monomers used in the creation of IPG gels. U.S. Pat. No. 4,169,036 describes a system for loading slab-gel holders for electrophoresis separation. U.S. Pat. No. 4,594,064 discloses an automated apparatus for producing gradient gels. Hence, use of a computer-controlled gradient maker in manufacturing IPG and other gels is known in the art.

One alternative method of running IPG strips in an IsomorpH device is disclosed in Disclosure Document No. 342751 (Anderson, N. L., entitled "Vertical Method for Running IPG Gel Strips"). The disclosed device uses sample wells pressed against the gel surface, but otherwise completely closed, so that the assembly could be rotated into a vertical orientation, thus allowing closer packing of gels and a greater gel capacity in a small instrument footprint. Additional methods are disclosed in Disclosure Document No's. 393753 (Anderson, N. L., Goodman, Jack, and Anderson, N. G., entitled "Gel Strips for Protein Separation") and 412899 (Anderson, N. L., Goodman, Jack, and Anderson, N. G., entitled "Automated System for Two-Dimensional Electrophoresis").

Systems for making non-planar slab gels are also known in the art and are disclosed in the following references: U.S. Pat. No. 5,074,981 discloses a substitute for submarine gels using an agarose block that is thicker at the ends and hangs into buffer reservoirs. U.S. Pat. No. 5,275,710 discloses lane-shaped gels formed in a plate and gel-filled holes extending down from the plate into buffer reservoirs. These gel systems, however, do not provide a gel which can be given a cross-section that is optimal for producing high-resolution protein separation. Furthermore, these systems cannot incorporate varying cross-sections along the length of a gel as required.

SDS Slab Gel Electrophoresis

Charged detergents such as sodium dodecyl sulfate (SDS) can bind strongly to protein molecules and "unfold" them into semi-rigid rods whose lengths are proportional to the length of the polypeptide chain, and hence approximately proportional to molecular weight. A protein complexed with such a detergent is itself highly charged (because of the charges of the bound detergent molecules), and this charge causes the protein-detergent complex to move in an applied electric field. Furthermore, the total charge also is approximately proportional to molecular weight (since the detergent's charge vastly exceeds the protein's own intrinsic charge), and hence the charge per unit length of a protein-SDS complex is essentially independent of molecular weight. This feature gives protein-SDS complexes essentially equal electrophoretic mobility in a non-restrictive medium. If the migration occurs in a sieving medium, such as a polyacrylamide gel, however, large (long) molecules will be retarded compared to small (short) molecules, and a separation based approximately on molecular weight will be achieved. This is the principle of SDS electrophoresis as applied commonly to the analytical separation of proteins.

An important application of SDS electrophoresis involves the use of a slab-shaped electrophoresis gel as the second dimension of a two-dimensional procedure. The gel strip or cylinder in which the protein sample has been resolved by isoelectric focusing is placed along the slab gel edge and the molecules it contains are separated in the slab, perpendicular to the prior separation, to yield a two-dimensional (2-D) separation. Fortunately, the two parameters on which this 2-D separation is based, namely isoelectric point and mass, are almost completely unrelated. This means that the theoretical resolution of the 2-D system is the product of the resolutions of each of the constituent methods, which is in the range of 150 molecular species for both IEF and SDS electrophoresis. This gives a theoretical resolution for the complete system of 22,500 proteins, which accounts for the intense interest in this method. In practice, as many as 5,000 proteins have been resolved experimentally. The present invention is aimed primarily at the 2-D application, and includes means for automating the second dimension SDS separation of 2-D process to afford higher throughput, resolution and speed.

It is current practice to mold electrophoresis slab gels between two flat glass plates, and then to load the sample and run the slab gel still between the same glass plates. The gel is molded by introducing a dissolved mixture of polymerizable monomers, catalyst and initiator into the cavity defined by the plates and spacers or gaskets sealing three sides. Polymerization of the monomers then produces the desired gel media. This process is typically carried out in a laboratory setting, in which a single individual prepares, loads and runs the gel. A gasket or form comprising the bottom of the molding cavity is removed after gel polymerization in order to allow current to pass through two opposite edges of the gel slab: one of these edges represents the open (top) surface of the gel cavity, and the other is formed against its removable bottom. Typically, the gel is removed from the cassette defined by the glass plates after the electrophoresis separation has taken place, for the purposes of staining, autoradiography, etc., required for detection of resolved macromolecules such as proteins.

The concentrations of polyacrylamide gels used in electrophoresis are stated generally in terms of %T (the total percentage of acrylamide in the gel by weight) and %C (the proportion of the total acrylamide that is accounted for by the crosslinker used). N,N'-methylenebis acrylamide ("bis") is typically used as crosslinker. Typical gels used to resolve proteins range from 8%T to 24%T, a single gel often incorporating a gradient in order to resolve a broad range of protein molecular masses.

In most conventional systems used for SDS electrophoresis, use is made of the stacking phenomenon first employed in this context by Laemmli, U. K. (1970) *Nature* 227, 680. In a stacking system, an additional gel phase of high porosity is interposed between the separating gel and the sample. The two gels initially contain a different mobile ion from the ion source (typically a liquid buffer reservoir) above them: the gels contain chloride (a high mobility ion) and the buffer reservoir contains glycine (a lower mobility ion, whose mobility is pH dependent). All phases contain Tris as the low-mobility, pH determining other buffer component and positive counter-ion. Negatively charged protein-SDS complexes present in the sample are electrophoresed first through the stacking gel at its pH of approximately 6.8, where the complexes have the same mobility as the boundary between the leading (Cl-) and trailing (glycine-) ions. The proteins are thus stacked into a very thin zone "sandwiched" between Cl- and glycine-zones. As this stacking boundary reaches the top of the separating gel the proteins become unstacked because, at the higher separating gel pH (8.6), the protein-SDS complexes have a lower mobility. Thus, in the separating gel, the proteins fall behind the stacking front and are separated from one another according to size as they migrate through the sieving environment of the lower porosity (higher %T acrylamide) separating gel. In this environment, proteins are resolved on the basis of mass.

Pre-made slab gels have been available commercially for many years (e.g., from Integrated Separation Systems). These gels are prepared in glass cassettes much as would be made in the user's laboratory, and shipped from a factory to the user. More recently, methods have been devised for manufacture of both slab gels in plastic cassettes (thereby decreasing the weight and fragility of the cassettes) and slab gels bonded to a plastic backing (e.g., bonded to a Gelbond® Mylar® sheet or to a suitably derivatized glass plate). To date, all commercially-prepared gels are either enclosed in a cassette or bonded to a plastic sheet on one surface (the other being covered by a removable plastic membrane). Furthermore, all commercially-prepared gels have a planar geometry.

Current practice in running slab gels involves one of two methods. A gel in a cassette is typically mounted on a suitable electrophoresis apparatus, so that one edge of the gel contacts a first buffer reservoir containing an electrode (typically a platinum wire) and the opposite gel edge contacts a second reservoir with a second electrode, steps being taken so that the current passing between the electrodes is confined to run mainly or exclusively through the gel. Such apparatus may be "vertical" in that the gel's upper edge is in contact with an upper buffer reservoir and the lower edge is in contact with a lower reservoir, or the gel may be rotated 90° about an axis perpendicular to its plane, so that the gel runs horizontally between a left and right buffer reservoir, as is disclosed in U.S. Pat. No. 4,088,561 (e.g., "DALT" electrophoresis tank). Various configurations have been devised in order to make these connections electrically, and to simultaneously prevent liquid leakage from one reservoir to the other (around the gel).

When used as part of a typical 2-D procedure, an IEF gel is applied along one exposed edge of such a slab gel and the proteins it contains migrate into the gel under the influence of an applied electric field. The IEF gel may be equilibrated with solutions containing SDS, buffer and thiol reducing agents prior to placement on the SDS gel, in order to ensure that the proteins the IEF gel contains are prepared to begin migrating under optimal conditions, or else this equilibration may be performed in situ by surrounding the gel with a solution or gel containing these components after it has been placed in position along the slab's edge.

A slab gel affixed to a Gelbond® sheet is typically run in a horizontal position, lying flat on a horizontal cooling plate with the Gelbond® sheet down and the unbonded surface up. Electrode wicks communicating with liquid buffer reservoirs, or bars of buffer-containing gel, are placed on opposite edges of the slab to make electrical connections for the run, and samples are generally applied onto the top surface of the slab (as in the instructions for the Pharmacia ExcelGels).

It is current practice to detect proteins in 2-D gels either by staining the gels or by exposing the gels to a radiosensitive film or plate (in the case of radioactively labeled proteins). Staining methods include dye-binding (e.g., Coomassie Brilliant Blue), silver stains (in which silver grains are formed in protein-containing zones), negative stains in which, for example, SDS is precipitated by Zn ions in regions where protein is absent, or the proteins may be fluorescently labeled. In each case, images of separated protein spot patterns can be acquired by scanners, and this data reduced to provide positional and quantitative information on sample protein composition through the action of suitable computer software.

Additional methods are disclosed in Disclosure Document No's. 393754 (Anderson, N. L., Goodman, Jack, and Anderson, N. G., entitled "Apparatus and Methods for Casting and Running Electrophoresis Slab Gels") and 412899 (Anderson, N. L., Goodman, Jack, and Anderson, N. G., entitled "Automated System for Two-Dimensional Electrophoresis").

Sample Preparation

Protein samples to be analyzed using 2-D electrophoresis are typically solubilized in an aqueous, denaturing solution such as 9M urea, 2% NP-40 (a non-ionic detergent), 2% of a pH 8–10.5 ampholyte mixture and 1% dithiothreitol (DTT). The urea and NP-40 serve to dissociate complexes of proteins with other proteins and with DNA, RNA, etc. The ampholyte mixture serves to establish a high pH (~9) outside the range where most proteolytic enzymes are active, thus preventing modification of the sample proteins by such enzymes in the sample, and also complexes with DNA present in the nuclei of sample cells, allowing DNA-binding proteins to be released while preventing the DNA from swelling into a viscous gel that interferes with IEF separation. The purpose of the DTT is to reduce disulfide bonds present in the sample proteins, thus allowing them to be unfolded and assume an open structure optimal for separation by denaturing IEF. Samples of tissues, for example, are solubilized by rapid homogenization in the solubilizing solution, after which the sample is centrifuged to pellet insoluble material and DNA, and the supernatant collected for application to the IEF gel.

Because of the likelihood that protein cysteine residues will be come oxidized to cysteic acid or recombine and thus stabilize refolded, not fully denatured protein structures during the run, it is desirable to chemically derivatize the cysteines before analysis. This is typically accomplished by alkylation to yield a less reactive cysteine derivative.

Use of 2-D Electrophoresis

Two-dimensional electrophoresis is widely used to separate from hundreds to thousands of proteins in a single analysis, in order to visualize and quantitate the protein composition of biological samples such as blood plasma, tissues, cultured cells, etc. The technique was introduced in 1975 by O'Farrell, and has been used since then in various forms in many laboratories.

Spot Cutter

One device that may be used in processing electrophoresis gel is a spot cutter machine that excises regions of a two-dimensional electrophoresis gel. The excised regions may contain macromolecules that have been separated due to electrophoresis. The excised regions may, therefore, be retained and used to analyze the macromolecular components of the excised region.

A prior art spot cutter is shown in U.S. Pat. No. 6,064,754 to Parekh et al. The Parekh patent shows a spot cutter that is designed to work with a two-dimensional electrophoresis gel bonded to a glass plate or other substrate in order to provide spatial stability. Parekh, at col. 6, lines 1–31 teaches away from using a non-supported electrophoresis gel. Therefore, the spot cutter of Parekh must work on this glass plate or substrate. In addition to cutting or excising the spot, the cutter of Parekh must separate the excised portion from the underlying substrate. Since the gel is bonded to the substrate, this poses an additional problem.

Parekh, in column 14, lines 1–7, discloses that in addition to punching down through the electrophoresis gel, the spot cutter includes multi-directional side-to-side tip movement on the substrate in order to break the bond between the gel and the substrate. This, of course, means additional steps and more likelihood of damaging the excised region, damaging the gel around the excised region, or disturbing the macromolecular components contained therein.

Another purpose of the glass substrate of Parekh is to provide a reference frame. Once the glass and gel is scanned, the outer perimeter of the glass substrate may be used to guide the spot cutting operation.

The gel systems known in the art or referenced above, however, do not provide an integrated, fully automated, high-throughput system for two-dimensional electrophoresis of proteins. Moreover, current IPG and slab gel systems are not fully automated, wherein all operations including gel casting, processing, sample loading, running and final disposition are carried out by an integrated, fully automated system. Current gel systems cannot be fully controlled by a computer and cannot systematically vary gel, process, sample load and run parameters, provide positive sample identification, and cannot collect process data with the object of optimizing the reproducibility and resolution of the protein separations.

OBJECT OF THE INVENTION

It is an object of the present invention to provide means for fully automated, high-throughput two-dimensional electrophoresis of proteins.

It is a further object of the present invention to provide a means of alkylating protein sulfhydryl groups in an automated manner.

It is a further object of the present invention to provide an IPG gel system optimized for use in a two-dimensional gel system wherein all operations including gel casting, processing, sample loading, running and final disposition (either by staining for protein detection or application to a second dimension slab gel for use in a two-dimensional protein separation) are carried out by an automated system.

It is a further object of the present invention to provide an IPG gel which is not restricted to a planar geometry, but which instead can be given any cross-section judged optimal for producing a high-resolution protein separation, and can incorporate varying cross-sections along its length as required.

It is a further object of the present invention to provide an IPG gel strip system that can be fully controlled by a computer, thereby affording the opportunity to systematically vary gel, process, sample load and run parameters and collect process data with the object of optimizing the reproducibility and resolution of the separation.

It is a further object of the present invention to provide a system for SDS slab gel electrophoresis offering facile automation (the slab gels should be easily handled in a robotic manner during casting, loading and running).

It is a further object of the present invention to provide accurate placement of the sample with respect to the plane of the slab gel, so as to avoid migration of sample macromolecules in a distribution that is asymmetric with respect to the plane of the slab gel, i.e., along one surface.

It is a further object of the present invention to provide effective and even cooling of the slab gel surface so that voltage (and hence heat generated) can be increased, with attendant improvements in gel resolution (due to shorted run times, and consequently decreased diffusion time).

It is a further object of the invention to provide facile automation of slab gel staining and scanning.

It is a further object of the invention to provide automated means for the recovery of selected protein spots or gel zones for the purpose of protein identification and characterization by means such as microchemical sequencing or mass spectrometry.

SUMMARY OF THE INVENTION

The present invention provides an integrated, fully automated, high-throughput system for two-dimensional electrophoresis comprised of gel-making machines, gel processing machines, gel compositions and geometries, gel handling systems, sample preparation systems, software and methods. The system is capable of continuous operation at high-throughput, to allow construction of large quantitative data sets.

Sample Preparation

Automated means are provided for treatment of protein-containing samples to effect the reduction and alkylation of cysteine sulfhydryl groups contained therein, with the object of preventing protein loss in the 2-D process through protein aggregation or refolding associated with sulfhydryl re-oxidation during the run.
IEF IPG gels are cast in a computer-controlled mold system capable of repeatedly casting a gel on a film support, advancing the support, cutting off the strip of support carrying the fresh gel, and presenting the strip to a robotic arm. The robotic arm subsequently carries the IPG strip and inserts it in a sequence of processing stations that implement steps required to prepare the IPG and use it, including washing, drying, rehydration, sample loading, and subjection to high voltage.

The approach used in casting the IPG gel allows the shape of the gel to depart from conventional flat planar strip geometry. The method of sample loading allows the sample to be applied over a large area of the gel. Such a gel format can provide an improved two-stage separation system: a first stage in which the proteins are separated in a minimally-restrictive, ideally fluid medium by isoelectric focusing in a channel or surface layer containing conventional ampholytes but surrounded by an IPG gel that establishes the pH gradient, and continuing on to a second stage in which the proteins are imbibed by the surrounding IPG gel at, or near their isoelectric points and maintained in stable, focused positions until the end of the run.
SDS Slabs SDS slab gels used for the second dimension separation are formed in an automated mold which plays the role of the gel-forming cassette of a conventional system. By using an approach analogous to injection molding, the gel is no longer required to assume a homogeneous planar configuration. In effect, a three-phase gel may be constructed, having regions corresponding to the separating gel, stacking gel and upper buffer reservoirs of a conventional slab gel system. Polymerizable gel solutions can be fed to the mold by one or more computer-controlled pumping devices, thus facilitating the creation of multiple zones of gel having different electrochemical properties. An upper electrode in the form of a rigid bar is polymerized into one region of the slab gel, allowing it to be manipulated and transported "bare" (i.e., without any surface protection or coating) by a second robotic arm (i.e., no cassette).

A slot or other means is provided for introducing a sample (usually in the form of a first dimension gel rod or strip) into or onto the slab. The slab is "run" (voltage applied) while it is hanging in a bath of cooled, circulating insulating liquid, such as silicone oil. The oil prevents evaporation of water from the planar gel surfaces as the gel runs (a function typically performed by the glass plates of a conventional gel cassette) and prevents joule heat caused by the electrophoresis current from raising the temperature of the gel appreciably. The gel contacts a layer of aqueous solvent underlying the oil, serving as a lower buffer (with suitable electrodes). The low density of the oil keeps it above and unmixed with the lower aqueous buffer.

After the run, the slab gel is carried by the second robotic arm to a succession of tanks containing a series of solutions needed to effect staining of the protein spots or bands on the gel. Because of differences in the physical densities of these solutions, the staining can make use of the fact that, as solutes are exchanged between the hanging gel slab and the solution, a lamina forms at the surfaces of the slab gel that has a density different from that of the bulk solvent. Because of this difference, the fluid in this lamina either rise's or falls as a curtain along the slab surface, and is replaced by fresh solvent. Hence, depleted solution accumulates at either the top or bottom of the tank, where it can be removed and replaced with fresh solution. After staining, the gel can be transported by the robotic arm to a scanner where it can be digitized for computer analysis.
Software The entire process can be controlled by a computer running software that both drives the creation and processing of each gel and collects process data from sensors placed at strategic points in the production line so as to allow quality control and optimization. A scheduling algorithm is implemented in software so that each sample can be run with different gel parameters, if desired, while ensuring that the manifold actions required to process one sample do not interfere with actions required to process other gels in the system (e.g., so that the arm used to transport IPG gels between processing stations is not required to be in two places at once).

BRIEF DESCRIPTION OF THE DRAWINGS

FIG. 5 shows a series of six alternative cross-sections for IPG gels formed by various mold activities.

FIGS. 23A–23E show detail and operation of the spot cutter head.

DETAILED DESCRIPTION OF THE EMBODIMENTS

Figure 1:
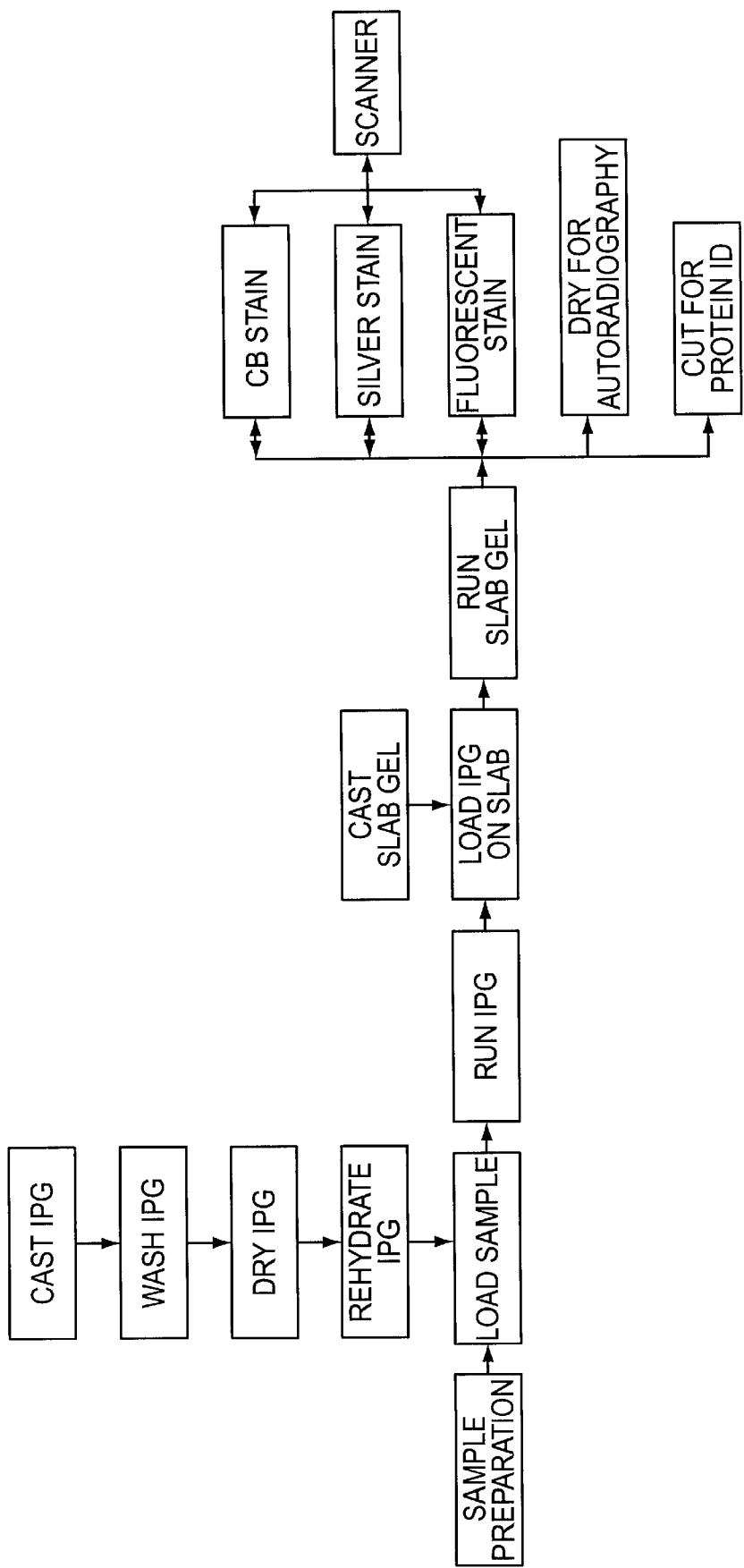
FIG. 1 is a schematic diagram of the entire automated 2-D electrophoresis process.

The preferred embodiment of the automated system for 2-D electrophoresis described is a continuously-operating production line, making each gel (both IEF and SDS) just as needed, and capable of undertaking all steps of the process (FIG. 1)—from loading of sample onto the first dimension gel to final entry of protein quantitation data into a computer database.

Sample Preparation

In order that proteins retain constant chemical properties during the process of separation by IPG-IEF and SDS electrophoresis, it is important that the sulfhydryl (SH) groups of the cysteine residues that they contain not be allowed to reform disulfide bridges or become oxidized to cysteic acid during the separation process. In the preferred embodiment, the protein cysteine residues are permanently rendered stable by alkylation with iodoacetamide or one of its uncharged or zwitterionic derivatives (such as S+2-amino-5-iodoacetamido-pentanoic acid), which introduces a very hydrophilic group at every cysteine position but does not change the protein's net charge or apparent isoelectric point and has a negligible effect on protein mass. This derivatization is implemented in an automated fashion using a size exclusion gel filtration column to exchange the proteins out of the initial sample solubilization solution, through a reagent zone containing alkylating reagent, and finally into a medium suitable for application to an IPG gel. The size exclusion media is chosen so as to exclude proteins but not low molecular weight solvents (e.g., polyacrylamide beads such as BioRad P-6 BioGel). In practice, a sample containing a sulfhydryl reducing reagent such as DTT is removed from a vial selected by a conventional autosampler such as is used in high performance liquid chromatography (HPLC), directed by a valve at the head of the column onto a column which has been pre-equilibrated with the final sample solvent and a zone (immediately preceding the sample) containing alkylating reagent in sufficient excess to ensure rapid reaction with protein cysteines. Once the sample zone is loaded, the valve switches to deliver a stream of final sample solvent that propels all the zones down the column and prepares the column for the succeeding cycle. As the initial sample zone moves down the column the protein molecules, because of their greater size, fail to penetrate into the particles of the column packing and hence move forward at a greater speed than that of the bulk solvent, which freely exchanges into the volume of the porous particles. This principle of separation is well known in the art. The proteins thus move into the zone of alkylating reactant, react there, and finally move even farther forward into the preceding zone of final sample solvent. This procedure thus ensures alkylation of protein sulfhydryls and removal of any low molecular weight contaminants as well. The sample is then ready for application to an IPG gel.

Figure 2:
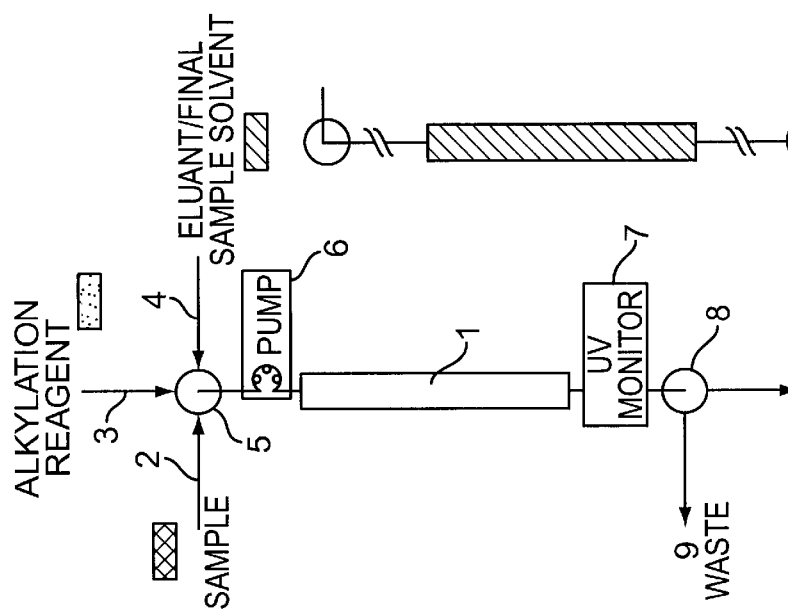
FIG. 2 illustrates sample preparation using a size exclusion column.

FIG. 2 illustrates a sample preparation apparatus which uses a size exclusion column. Diagram A depicts the arrangement of the components of the sample preparation apparatus. A size exclusion column 1 is connected to one of a series of input liquid streams 2, 3 and 4 by a multi-position switching valve 5, with liquid flow into the column driven by pump 6. Initially column 1 is equilibrated with liquid 4. Input 2 delivers the crude sample from a conventional autosampler or other device. Input 3 delivers a stream of reagent required to effect a chemical treatment of the sample proteins (typically a sulfhydryl alkylating reagent), and input 4 delivers a stream of column eluent (the solvent in which the sample proteins will ultimately emerge). Liquid emerging from the size exclusion column flows through a UV absorbance or other column monitor flow cell 7 and thereby to a multiport valve 8 that directs the eluent either to waste 9 or to a sample collection vessel 10.

Diagrams B through H depict steps in the operation of the column to effect sample protein derivatization. In diagram B, the column 1 is equilibrated with eluent through connection of its input to eluent reservoir 4 by input valve 5, and its output to waste 9 by output valve 8. Pump 6 and UV monitor 7 are not shown for clarity: the pump is assumed to remain on during the sequence of operations, delivering liquid continuously through the column. In C, a zone of alkylation reagent 11 is introduced onto the column by switching the input valve 5 to draw solvent from the alkylation reagent reservoir 3. In diagram D, a zone of sample is introduced after the alkylating reagent zone, said sample zone comprising a solvent phase 12 and a protein solute phase 13. In diagram E, input to the column once again switches to eluent, pushing the sample and alkylation zones down the column.

As the sample solvent zone moves down the column, the proteins it initially contained are excluded from the matrix of the size exclusion column and hence advance into the alkylation zone (a well known feature of such columns when used in desalting applications). During this period, the proteins are exposed to the alkylating reagents and their component sulfhydryl groups are alkylated to prevent re-folding of the proteins in subsequent stages of the 2D electrophoresis process. In diagram F, the proteins in solute phase continue to advance down the column faster than the proteins in solvent phase, and enter the leading region comprised of the first applied eluent phase. In diagram G, the alkylated proteins are collected by switching the output collection valve 8 to the sample collection position. In diagram H, continuing flow of eluent into the column forces the alkylation and initial sample solvent phases out of the column in preparation for the column's regeneration and re-use.

In an alternative embodiment, alkylation is performed with a negatively charged reagent such as iodoacetic acid, thereby substituting a negative charge at every alkylated protein sulfhydryl. When this reaction is accomplished stoichiometrically, very basic proteins containing cysteine residues are shifted towards more neutral isoelectric points, thereby facilitating their detection on IEF gels.

IPG

The first operation of the 2D gel procedure is creation of an isoelectric focusing gel to effect the first dimension separation. Such a separation is most effectively carried out in an immobilized pH gradient (IPG) gel, in which a gradient of polymerizable monomers is gelled to form a fixed spatial pH gradient.

Gradient

The compositional gradient required to form the desired pH gradient IPG gel can be produced by a system of four computer-controlled motorized syringes delivering, respectively, heavy gel monomer composition formulated to yield a basic pH, light gel monomer composition formulated to yield an acidic pH, a polymerization initiator such as ammonium persulfate, and a polymerization catalyst such as TEMED. A computer program constructed, for example, in the LabVIEW language, is used in conjunction with a computer and stepper motor control card (for example, a Compumotor AT6400 card) to produce a varying ratio between the speed of delivery of heavy and light components, while maintaining a continuous delivery of initiator and catalyst required for polymerization. Each of the four syringes is connected to a separate computer-controlled valve (e.g., a 6-port high pressure liquid chromatography valve in which each of two rotational positions connects a fixed input with one of two lines and a fixed output with one of two other lines) that allows connection of the syringe either to an external reservoir, or to the delivery tubing system. When the syringe is connected to the reservoir for refilling, the delivery system is connected to a source of pressurized flush solvent (typically water) that displaces polymerizable monomer solutions from the delivery tubes to prevent blockage. In the delivery tubing system, the four component flows emerging from the four valves are combined by appropriate tubing junctions to yield one mixed fluid stream routed into the gradient delivery tube in the mold.

An additional fifth syringe may be added to supply a third polymerizable monomer solution of density and pH intermediate between the light and heavy monomer solutions, for the purpose of creating very wide pH gradients as a sequence of two two-component gradients (i.e., A→B followed by B→C).

Figure 3:
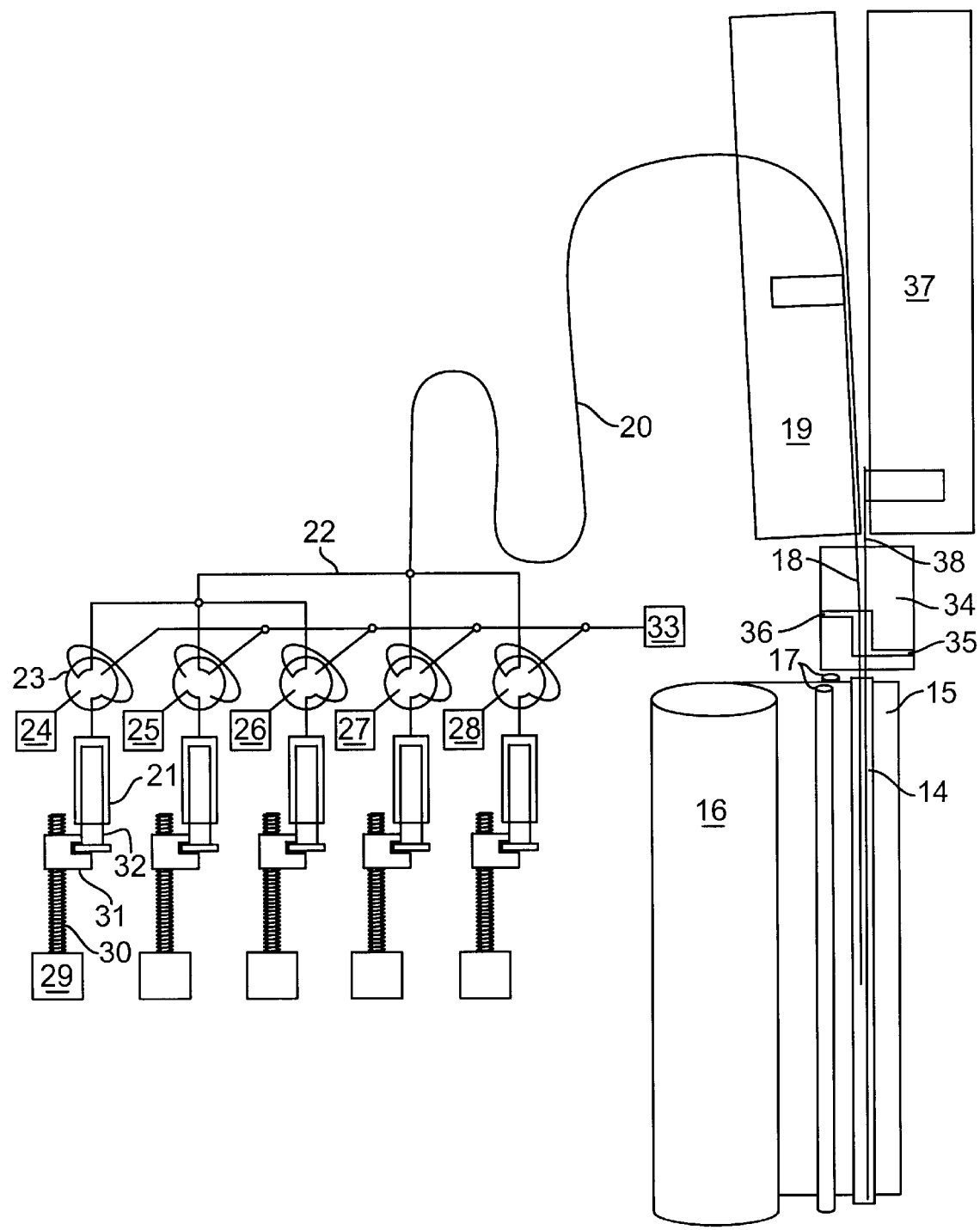
FIG. 3 illustrates an IPG gradient maker and mold system.

FIG. 3 schematically depicts the components of an IPG casting system. A vertically-oriented mold cavity is formed of a front mold half 14 and a back surface comprised of activated Gelbond® sheet 15. At each casting cycle, fresh Gelbond® is delivered to the mold from a roll 16 through motorized transport rollers 17. A small diameter rigid delivery tube 18 extends into the mold from the top and may be raised out of the mold by linear motion 19. A flexible tube 20 delivers a polymerizable composition to the delivery tube from a gradient maker having five computer controlled syringes. Each syringe 21 is connected to the output manifold 22 through a 6-port valve 23 allowing the syringe to be connected either to a liquid reservoir (e.g., liquid reservoir 24) for refilling or to the output manifold. These syringes deliver one of three acrylamide monomer solutions (24, 25, 26) ammonium persulfate 27 and TEMED 28. Valves attached to syringes drawing from reservoirs 24, 26, 27 and 28 are shown in delivery position, while the valve attached to the syringe drawing from reservoir 25 is shown in refill position.

Each syringe is driven by a motor 29 rotating a lead screw 30 that generates linear motion of a block 31 attached to the syringe's plunger 32. During the refilling of syringe 21 from its associated reservoir 24, the associated 6-port valve 23 connects the output manifold 22 to a pressurized source of non-polymerizable solvent 33 (e.g., water), to purge the manifold and delivery tubes of polymerizable media (this configuration shown for the middle syringe connected to reservoir 25). After delivering a gradient of polymerizable monomers to the mold, the delivery tube 18 is raised by delivery tube motion 19 so that its open end lies in a block 34 through which air is sucked at high velocity by an air pump, from input 35 to output 36. A second linear motion 37 carries a long straight pin 38 which can be inserted into the mold along its axis or raised out of it.

The resulting compositional gradient must be delivered into a suitable mold such that a spatial gradient is maintained during gelation. In order to achieve this, the delivery tube delivering gel composition to the mold is arranged on a vertical linear transport capable of inserting the open end of the delivery-tube to the bottom of the vertical mold cavity, and raising it slowly as the gradient is dispensed so as to deposit successive elements of the gradient above one another (at the rising meniscus of the liquid in the mold). When the gradient is thus completed, the delivery tube is raised fully out of the mold and into a suction block 34 mounted just above the gel mold. In this position, liquid emerging from the delivery-tube is sucked into a perpendicular waste tube by the action of a vacuum, thereby providing a waste path for flush solvents directed through the delivery-tube between gradient dispensing operations in order to prevent blockage of the tube by any remaining polymerizable components.

Suitable compositions for the four components combined to make an IPG are as follows. Solutions of polymerization catalyst and initiator (assuming that each comprises 10% of the total volume dispensed) are, respectively, 1.2% tetramethylethylenediamine (TEMED) and 1.2% ammonium persulfate (AP), both in water. The two solutions of polymerizable monomers (whose proportions in the output stream vary to yield a gradient of titratable monomers and physical density) may be made up as shown in the following Table to achieve a gradient over a range of pH 4 to 9. The titratable monomers used are Immobilines® manufactured by Pharmacia Biotech. Glycerol and deuterium oxide (heavy water) are used to increase the density of one of the solutions, thus helping to stabilize the gradient formed in the mold through the interaction of the resulting density gradient and the earth's gravity.

TABLE 1

|  | Heavy (pH 4) | Light (pH 9) |  |
|---|---|---|---|
| Immobiline pK 3.6 | 2,762 | 491 | microliters |
| Immobiline pK 4.6 | 785 | 1,414 | microliters |
| Immobiline pK 6.2 | 773 | 1,200 | microliters |
| Immobiline pK 7 | 75 | 988 | microliters |
| Immobiline pK 8.5 | 834 | 236 | microliters |
| Immobiline pK 9.3 | 738 | 2,209 | microliters |
| 31.8% T, 5.6% C Acrylamide/bis in $H_2O$ | 0 | 9.83 | ml |
| 31.8% T, 5.6% C Acrylamide/bis in $D_2O$ | 9.83 | 0 | ml |
| Glycerol | 6.25 | 0 | ml |
| $D_2O$ (Heavy Water) | 19.79 | 0 | ml |
| Water | 0 | 25.46 | ml |
| 1 M Tris HCl, pH 7.0 | 8.17 | 8.17 | ml |
| Total | 50.00 | 50.00 | ml |

Because the volume of the tubing connecting the gradient maker with the mold is a significant fraction of the mold volume (even when narrow bore HPLC tubing and connectors of inside diameter 0.010" are used), it is necessary to take account of this volume when dispensing a gradient. Hence, the procedure adopted and implemented in the control software consists of five stages: 1) delivery of the first segment of the desired gradient, equal in volume to the volume of the delivery tube, for the purpose of replacing the flush solvent in the tube with polymerizable monomer; 2) insertion of the delivery tube into the mold; 3) delivery of the remainder of the gradient while the delivery tube is raised (withdrawn from the mold) at a speed such that the delivered gradient composition is emitted at the rising surface of the liquid in the mold; 4) following the gradient by a volume equal to the delivery tube volume of the final "light" composition, for the purpose of forcing the section of the gradient remaining in the delivery tube into the mold while the delivery tube continues to rise; and 5) removal of the delivery tube from the mold to the upper vacuum flush position where, following switching of the four valves, flush liquid is forced through the delivery tube system to remove polymerizable material and to prepare the system for a subsequent gradient:delivery.

Mold

In the preferred embodiment, the IPG is cast in a narrow vertical mold cavity formed by pressing a movable mold half against a sheet of Gelbond® PAG-activated plastic substrate which in turn is pressed against a fixed backing block whose temperature is controlled by circulation of chilled or heated water through internal cavities. The cavity in the movable mold half is surrounded on the sides and bottom by an O-ring groove with an O-ring to produce a liquid-tight seal against the Gelbond®. The Gelbond® substrate is made of Mylar® polyester plastic film treated in such a way as to produce on its active surface groups to which an acrylamide gel can bond covalently, thus attaching the gel to the Gelbond® substrate.

In the preferred embodiment, a longitudinal IPG gradient is formed in the cavity by dispensing a varying composition of gelable monomers into the cavity through a small diameter delivery tube. This delivery tube rises during the dispensing of the gradient, and consequent filling of the mold, so that the open end of the tube from which gelable monomer emerges is maintained at the rising level of the surface of the liquid dispensed into the mold. In addition, the gradient of gelable monomers is contrived so as to incorporate a physical density gradient that evolves from heavy to light during the dispensing of the gradient. Such a density gradient is produced by inclusion of a dense substance such as glycerol or deuterium oxide in place of a portion of the water present in the "heavy" gradient component. A density gradient dispensed in the "heavy" to "light" sequence from a tube maintained at the rising surface of liquid in the mold gives rise to a stable composition gradient in the mold which, when polymerized, yields an IPG.

Figure 4A:
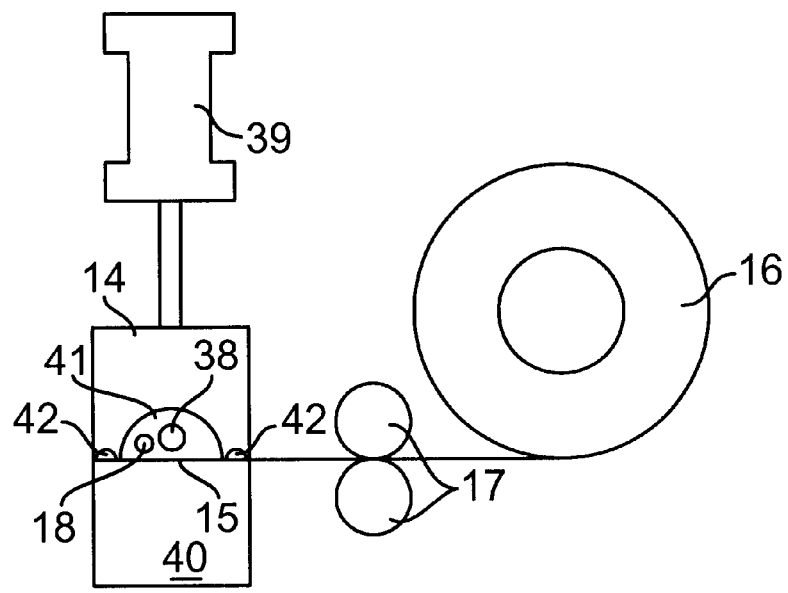
FIG. 4 is a schematic cross-section through an IPG mold system.
Figure 4B:
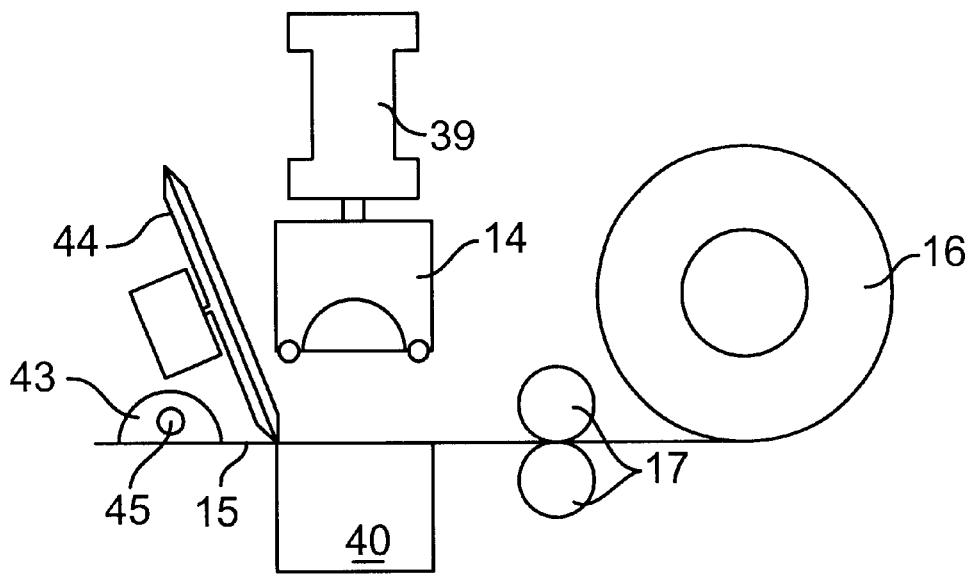

FIG. 4 is a schematic cross-section of an IPG mold system viewed from above (i.e., looking down into the mold cavity 14 depicted in FIG. 3). In diagram A, the front IPG mold half 14 is pressed against the Gelbond® sheet 15 by a pneumatic cylinder 39, whose pressure bears on a fixed back plate 40. In this example, the IPG mold cavity is of a semi-circular cross section 41. Lateral leakage of polymerizable components is prevented by linear O-rings 42. Mold temperature can be controlled by circulation of hot or cooled liquid through internal channels of the fixed back plate. Polymerizable components are introduced into the mold through moving delivery tube 18. A central hole may be formed in the IPG gel by polymerization with a pin 38 in place inside the mold cavity.

In diagram B of FIG. 4, following extraction of the delivery tube and pin from the mold, pneumatic cylinder 39 retracts the front IPG mold half 14, and rollers 17 cause the Gelbond® support 15 to slide laterally across the face of fixed back plate 40, thereby ejecting the IPG gel 43 on its Gelbond® substrate from the mold, in preparation for another cycle. A rotary blade 44 cuts the Gelbond® by moving vertically along the mold, thereby releasing a strip of Gelbond® carrying the newly-formed IPG gel. The gel produced has a longitudinal hole 45.

It is important to ensure that the gradient of the resulting gel reaches hydrostatic equilibrium (and hence proper gradient shape) before polymerization, and yet is fully polymerized (with complete incorporation of gelable monomers into the gel polymer matrix) before removal from the mold. This result is achieved by increasing the temperature in the mold after an initial gradient formation period: gelation proceeds much faster at higher temperature. In a typical protocol, the gel gradient is introduced at a temperature of 20° C. and after a period of approximately 4 minutes, during which the polymerizable monomers gel into a non-convecting state, the temperature in the mold is increased to approximately 50° C. by circulation of heated water through closed channels provided in the backing plate. After removal of the gel from the mold, the temperature is lowered to 20° C. by switching the circulation system to a chilled water supply in preparation for the next cycle.

Once the gel is polymerized, the mold is opened and the IPG gel is transported by manipulation of the Gelbond® support to which it has become covalently attached during polymerization. The form of the gel is determined by the form of the mold in which it is cast, the simplest being a flat, rectangular strip on the surface of the Gelbond®.

In a further embodiment, the gradient stream of polymerizable monomers is introduced into the mold cavity by means of a passage at the bottom of the cavity, in this case in the sequence light to heavy (opposite to the order when liquid is deposited at the rising surface of the liquid in the mold). A special valve is used to direct the flow of polymerizable liquid either into the mold or to waste, thereby allowing the contents of the delivery tubing to be purged of polymerizable components after casting of a gel.

Numerous alternative forms of the IPG gel can be produced. In one alternative embodiment, a pin is introduced into the mold before or during gel polymerization and slowly withdrawn afterwards, leaving a central hole down the length of the IPG gel. This can be accomplished by a procedure in which the pin is first rotated slowly, to reduce the adhesion of gel to the pin, and subsequently slowly withdrawn along its axis through the top of the mold. In another embodiment, a sample introduction channel or groove is formed at the exterior surface of the IPG gel by means of a suitably shaped ridge on the interior surface of the mold. The groove may be formed so as to be closed at its ends, thus forming a bounded depression, open only at the top. Provided that the gel is held horizontal during the run, i.e. with the groove in a horizontal plane and with its opening directed upward or to the side, then sample liquid placed in this groove will remain held there by capillary action, until imbibed by the gel or evaporated.

FIG. 5 shows a series of six alternative cross-sections for IPG gels formed by various mold cavities, after the strip has been cut from the Gelbond® roll. In diagram A, a semi-circular gel 43 with longitudinal hole 45 has been formed on the Gelbond® strip 46 and subsequently filled with sample. In diagram B, a semi-circular cross-section gel has a surface groove 47 in which sample is held by capillary action, while in diagrams C and D, other cross-sections with broader, flatter surface grooves 47 are shown, also holding sample by capillarity. In diagrams E and F, triangular and rectangular cross-sections without surface grooves are shown. In each case shown, the Gelbond backing material is wider than the gel itself, giving the strip greater stiffness and providing, particularly in E and F, a further form of cavity in which sample is held by capillarity: a groove created by the included angle between the side of the gel on one hand and the extended Gelbond substrate on the other.

In practice, the gel mold can be formed from any of a range of materials that do not inhibit polymerization of acrylamide, including glass, alumina, machinable ceramic, Ultem®, polysulfone, polystyrene, polycarbonate, polyurethane, acrylic, polyethylene or the like. For convenience in machining, and to allow observation of the mold's contents, a clear plastic such as polysulfone or acrylic is preferred.

Gelbond® Transport

Gelbond® substrate is advanced to the mold on repeated cycles from a large roll by feed rollers. After casting an IPG gel on the end of the Gelbond® (the IPG axis perpendicular to the length of the Gelbond® and parallel to the roll's axis), the strip of Gelbond® on which the gel is formed is cut from the roll using any of a variety of mechanical cutting mechanisms, including, for example, a rolling disk cutter of the type used to cut photographic paper, affixed to a vertical motion device. The resulting Gelbond® strip with IPG gel attached may then be grasped by any of a variety of mechanical or manual means for handling in further processing steps. In the preferred embodiment, the strip is 1.27 cm wide and approximately 65 cm long (the width of the Gelbond® substrate when provided in roll form). The IPG gel is 2 mm wide, 0.75 mm thick and 57 cm long (leaving 1.5 cm of the Gelbond® uncovered on either end of the strip).

Barcode Labeler

Preprinted barcoded labels are mechanically applied to each IPG-carrying strip on the side opposite the gel for identification purposes, although other labeling means known or available may be used.

Robotic Arm

A robotic arm system equipped with two pneumatically-activated pincers grasps the strip by the two ends to transport it between subsequent processing stations. The IPG arm system moves horizontally along a track, vertically along a linear table mounted on the track, and can rotate 90 degrees in order to pick up the IPG lying in a horizontal position and carry it in a vertical orientation to subsequent stations.

Sequence of IPG Processing Events

To employ a gel made by the procedure described above as the first dimension separation of a 2-D electrophoresis procedure, a sequence of processing operations, many of which have been well described in the art, is used to render the gel ready for use in a protein separation. These operations include removal of remaining unpolymerized monomers, initiator and catalyst by washing in deionized water; dehydration to remove incorporated water; and finally rehydration in a solution appropriate as a medium for protein separation. Subsequently, a protein-containing sample is applied to the gel, and the gel is subjected to a voltage gradient in order to separate the proteins along the gel length.

In the preferred embodiment, the IPG gel on its Gelbond® strip is gripped at both ends by the aforementioned movable arm and placed in one of a plurality of slots containing circulating purified water. After approximately two hours, most soluble materials remaining in the gel have diffused into the water and are thus removed from the gel.

The strip is then grasped again by the arm (which in the meantime may have moved to other positions to carry out other functions) and moved to a slot where it is subjected to a stream of air filtered so as to remove any contaminating particulate material (e.g., using a conventional HEPA filter). The gel is substantially dried in approximately 30 minutes.

Next, the arm again grasps the strip and moves it to a slot filled with rehydration solution, a medium typically consisting of 9 mole/liter urea, 2% of non-ionic detergent such as Nonidet P-40 or CHAPS, and 2% wide range, commercially-available ampholytes (e.g., BDH 3-10 ampholytes) in water. When samples are to be used whose protein SH groups have not been alkylated, 1% dithiothreitol is included in the rehydration solution as a sulfhydryl reducing agent. In a period of approximately two hours, the IPG gel is re-swollen in rehydration solution and ready to be used for protein separation. In order to prevent the formation of crystals due to evaporation at the surface of the rehydration solution bath, the rehydration solution is covered by a layer of light silicone oil, through which the IPG is inserted.

To carry out a protein separation, a volume of sample protein must be applied to the gel. In the preferred embodiment, sample protein in a solubilization solution similar in composition to the rehydration solution is applied on the surface of the IPG gel along its length. This application is effected by placing the IPG on a base plate with the gel face up, and depositing a stream of sample liquid onto the IPG gel surface from a needle held just above that surface, which is moved slowly along the length of the IPG as sample is pumped out. The resulting thin layer of protein-containing liquid on the IPG gel surface remains in place during subsequent manipulations of the gel strip so long as the axis of the gel remains in a horizontal plane (as is the case during movement using the arm system described). Means are provided for moving the needle up and down (to allow collection of sample by piercing the septum of a conventional septum-topped sample vial), and for moving it along the length of the IPG and farther, to positions where a sample vial may be placed and where the needle may be washed.

Figure 6:
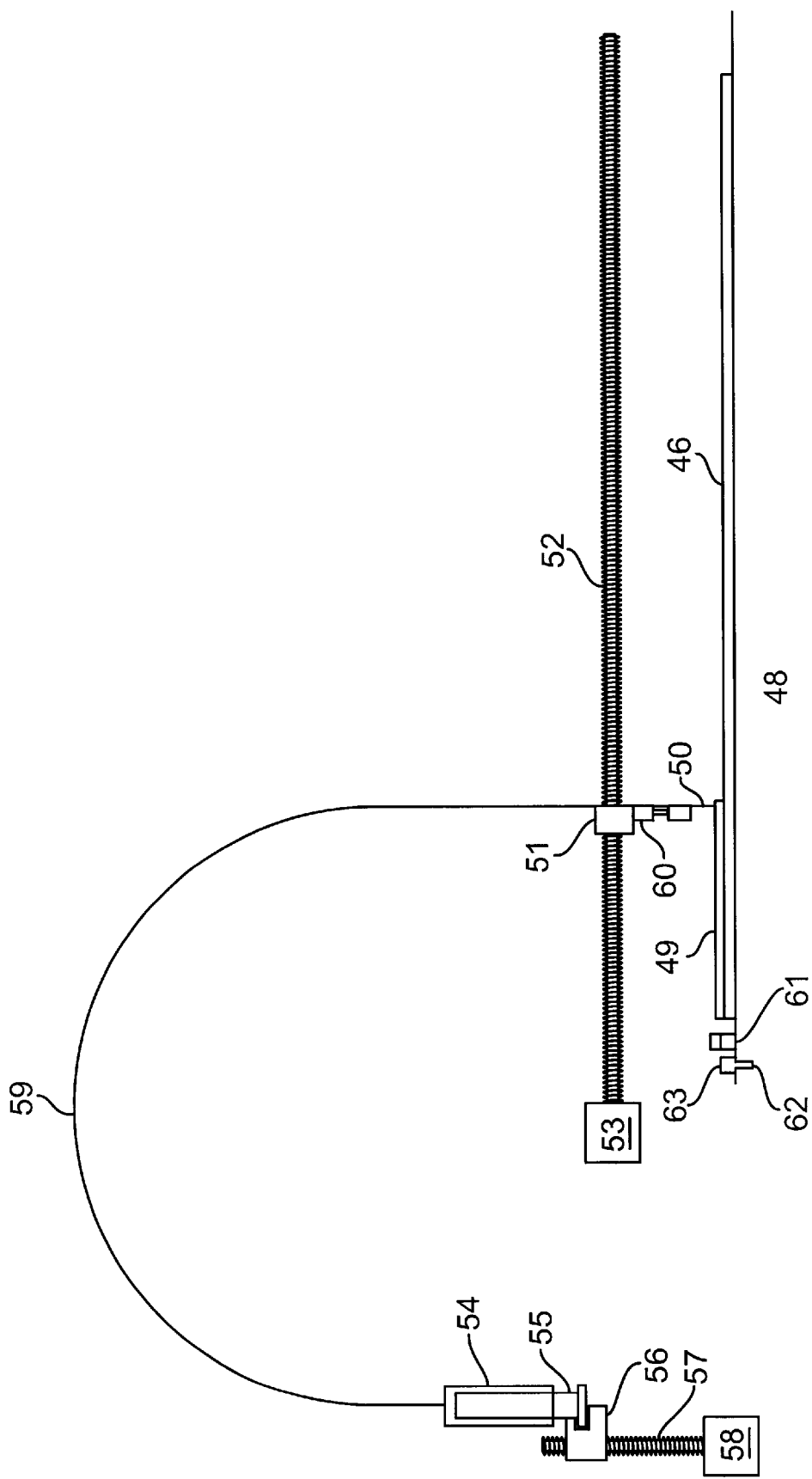
FIG. 6 is a schematic view of an IPG strip in a horizontal position with the gel-side on top of a base plate in position for sample loading.

FIG. 6 shows an apparatus for application of sample protein to an isoelectric focusing gel in accordance with the present invention. An IPG strip 46 lies horizontally, gel-side up, on a base plate 48. A trail of sample liquid 49 is left on the surface of the IPG gel as needle 50 discharges a steady stream of sample while moving along the IPG. The needle 50 is moved on carriage 51 through the action of lead screw 52 driven by motor 53. Sample flow is controlled by syringe 54 whose plunger 55 is moved by a block 56 which is in turn moved by a lead screw 57 turned by motor 58. Flexible tube 59 connects the syringe and the delivery needle. The sample is initially taken into the needle 50 and syringe 54 by raising the needle on its vertical pneumatic motion 60, driving the needle 50to the left, positioning it over sample vial 61, lowering the needle 50 to pierce the vial's septum top, withdrawing the sample through action of the syringe 54, raising the needle 50 again, moving into position over a gel strip, lowering the needle 50 and commencing synchronous motion of the syringe 54 and the needle carriage 51 to deposit the sample along the IPG surface. The needle 56 is washed between applications by positioning it over waste receptacle 62, where its exterior surface is washed by a jet of water 63.

In another embodiment, where a central hole is produced in the IPG gel during casting, the sample can be injected or peristaltically drawn into the channel prior to application of voltage along the gel. The sample liquid can be retained inside the channel by pinching the ends of the gel to close the channel, by injection of gas bubbles, or by various other means, including placing a drop of gelling material at both ends.

After sample loading, the gel strip is once again grasped by the arm and moved to one of a plurality of slots filled with a non-conducting oil (such as silicone oil) and having slotted carbon electrodes at either end positioned so as to contact the ends of the IPG gel. The oil may be circulated, cooled to ensure constant running temperature and sparged with a dry gas so as to eliminate oxygen and dissolved water. Since the resistance of the IPG gel rises during the run, slots maintained at a series of different voltages are provided, and the arm periodically moves the strip from one voltage to a higher voltage as the run progresses. In the preferred embodiment, a series of 6 voltage stages are provided, namely 1, 2.5, 5, 10, 20 and 40 kilovolts. The gel is maintained at each voltage for about 3 hours, except the last, where it rests until a second dimension slab gel is available. A total of 200,000 to 300,000 volt-hours may applied to each gel.

Slots such as those used for washing and for subsequent processing and running steps generally have clips at either end into which the gel strip is inserted by the arm, using a downward motion. When the grasping pincers at the ends of the arm release the Gelbond® strip, these clips continue to hold the strip extended between them by friction. In the preferred embodiment, these clips consist of a pair of parallel pins touching one another and projecting upwards from the floor of the slot. The strip is jammed between these pins during insertion into the slot, spreading them slightly and producing a friction fit. All the slots except the air dryer are contained at the sides and below to yield a liquid-tight vessel suitable for containing the liquid with which the IPG is to be treated at that stage. Slots used for application of high voltage also contain slotted carbon electrodes.

Figure 7:
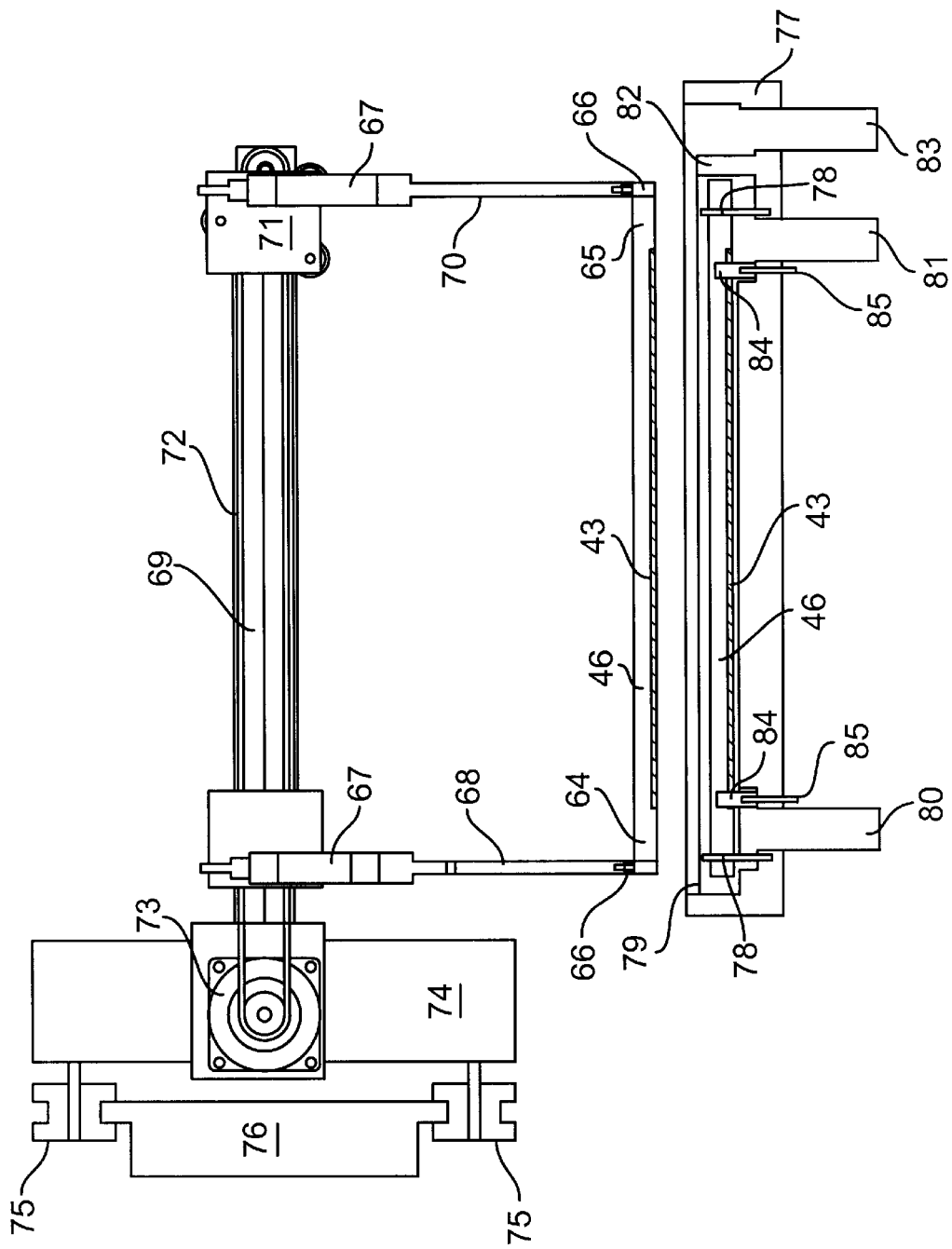
FIG. 7 is a side view of an IPG carrier arm and an IPG slot run.
Figure 8E:
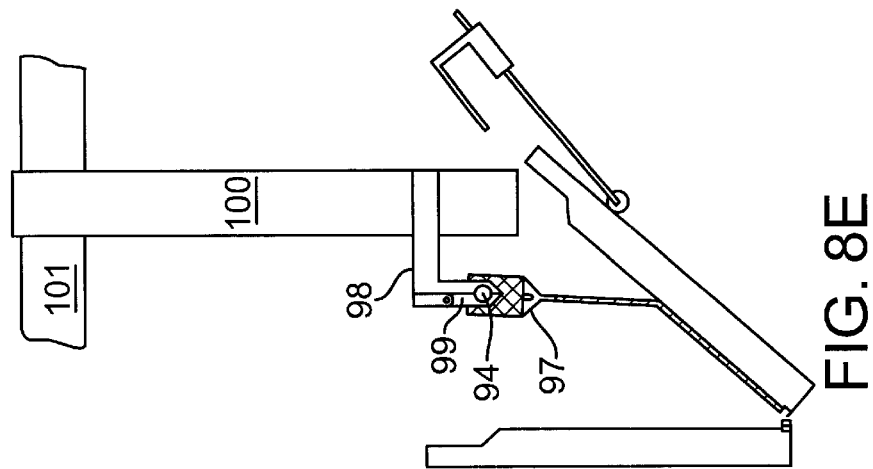
FIG. 8 illustrates the sequence of actions of a slab gel mold during casting operation.
Figure 8D:
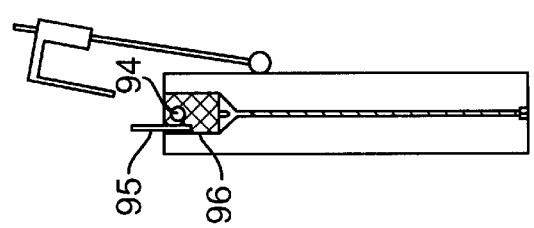
Figure 8C:
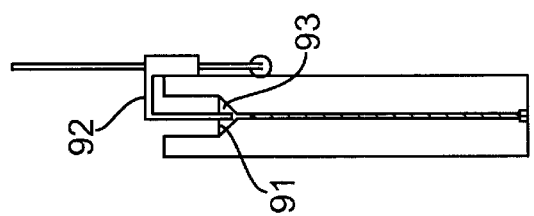
Figure 8B:
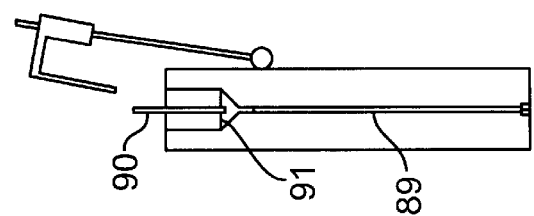
Figure 8A:
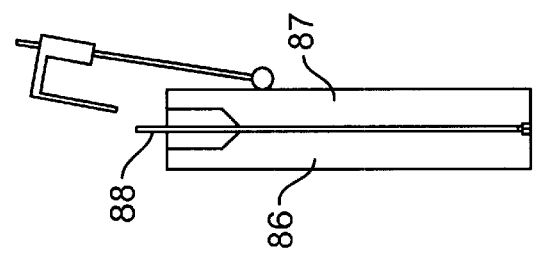

FIG. 7 shows a cross-section view of an IPG processing slot and the arm used to transport IPG strips between slots. A Gelbond® strip 46 carrying attached IPG gel 43 is held at its ends 64 and 65 by a distal arm 70 and a proximal arm 68, each carrying a gripper 66 actuated by a pneumatic cylinder 67. Both arms are mounted on a horizontal bar 69. One of the arms, in this case the distal arm 70, is mounted to a carriage 71 capable of moving along bar 69 under the control of belt 72, which in turn is moved by motor and pulley 73. Since the other arm 68 is fixed to the horizontal bar 69, movement of arm 70 by the motor and pulley in an outwards direction serves to stretch strip 46, keeping it taut (and therefore straight) between grippers 66. A vertical motion 74 serves to raise and lower the entire arm and bar assembly, thus allowing insertion of IPG gels into, and removal of gels from, the slots. The vertical motion is itself carried on motor-driven wheels 75 which engage a track 76 to move the arm assembly to positions over a variety of slots.

Movement of the arm assembly downwards (by motion of vertical motion 74) causes gel strip 46 and attached IPG gel 43 to be inserted into a processing slot in plate 77. The strip is held at its ends between pairs of pins 78 projecting from the floor of the slot, and is inserted beneath the surface of liquid 79. This liquid can be circulated over the IPG strip by introducing liquid through inlet 80 and simultaneously withdrawing liquid through outlet 81. Excess liquid flows over a dam 82 to exit via overflow 83. In slots devoted to the IEF process (where voltage is applied across the gel) the ends of the IPG gel 43 contact slotted electrodes 84, which are connected in turn to conducting pins 85 that penetrate the bottoms of the run slots in a liquid-tight manner, allowing electrical connection to a power supply on the outside.

During the early stages of a separation run, under an applied electric field, proteins can migrate through the liquid phase of the applied sample along a pH gradient initially formed by the action of the ampholytes incorporated in the sample. Because the proteins are initially migrating through liquid, without the retardation associated with migration through a gel matrix, they can approach their isoelectric points more rapidly than in a system where the entire migration path is through IPG gel. However, if proteins remained in this liquid phase at the end of the run, they could be displaced from their isoelectric positions by subsequent gel handling steps. Hence, conditions are contrived so that, as the run progresses, sample-containing liquid is imbibed by the gel, progressively shrinking the channel so that at the end of the run the channel contains a negligible amount of liquid. This is achieved by allowing surface water to be slowly removed from the exterior surface of the gel during the run by, for example, immersion of the gel in circulated silicone oil that has-been dehydrated by sparging with a dry gas such as argon or nitrogen.

During gel dehydration, and consequent collapse of any liquid filled central sample channel, proteins enter the gel at positions near their respective isoelectric points. Thus, a mixture of different proteins will enter the gel at points distributed along the gel length, rather than at one site at the edge of a sample well, thereby avoiding the precipitation often observed when a complex mixture of proteins migrates together into the gel through a small gel surface area. Excess liquid is removed through the exterior gel surface, either to a dry gas phase or to a water-extracting, non-aqueous, non-conducting liquid phase such as silicone oil.

SDS Electrophoresis

Slab Gel Casting

In the preferred embodiment, a gel is formed in a computer-controlled mold system whose operation is shown diagrammatically (in cross-section) in FIG. 8. The mold is composed of two halves 86 and 87 which can be forced together to comprise a liquid-tight cavity open at the top. The form of the mold is such that the gel 89 formed therein has a large, thin planar region at the bottom (within which proteins will be separated: the "separating gel") and above the thin planar region a substantially wider region (the "top gel") joined to the thin region by a joining region of gradually increasing width. The function of the top gel is to provide a buffer reservoir as a source of ions during the electrophoresis separation, and a mechanical support from which the separating gel hangs during the run and subsequent steps. The joining region joins the separating and top gel regions and provides a gradually narrowing cross-section adapted for the focusing of protein zones using the stacking process disclosed in Laemmli (U.K., 1970, *Nature* 227, 680), in which the joining region is comprised of a stacking gel. In the preferred embodiment, the separating region has a thickness of about 1 mm, the top region has a thickness of about 2 cm, and the joining region gives rise to a smooth fillet between the separating and top gels. The vertical height of the separating gel is 30 cm and that of the top gel is 5 cm. All gel regions have the same width, namely 60 cm.

Mixtures of polymerizable gel monomers are introduced into the closed mold by means of three tubes 88, 90 and 95 which can be made to extend down into the mold cavity from above. The first delivery tube 88 can be caused to extend to the bottom of the mold and is used to introduce a liquid stream that polymerizes to yield the separating gel 89. A second delivery tube 90 can be made to extend down inside the upper, wider section of the gel mold, and is used for the introduction of the second gel phase (the stacking gel 91) and (by means of switching a valve) an equilibration solution used to bathe the IPG applied to the slab gel. A third delivery tube 95 also can be made to extend into the upper section of the gel mold, and is used to introduce the liquid that polymerizes into the top reservoir gel phase.

A slot form 92 can be lowered into the open top of the mold cavity by vertical movement of the slot form. The mold can be opened by means of another movement, whereby one face of the mold pivots along a line near to and parallel with the bottom horizontal edge of the mold cavity to expose the gel. The mold cavity contains indentations at either end shaped so as to receive and support the ends of a carbon electrode rod 94 and suspend it inside the top gel volume during its polymerization. After polymerization of the gel, electrode rod 94 serves as both an upper electrode required for the electrophoresis separation and a mechanical support from which the gel hangs during subsequent handling and manipulation. A further controlled motion is provided to clamp the electrode rod to one face of the gel mold, thus ensuring that the gel will always be recovered in a fixed location after the mold is opened.

FIG. 8 illustrates the sequence of actions of slab gel mold during the casting operation. In configuration A, a slab gel mold comprised of a fixed mold half 86 and a movable mold half 87 is shown in the closed position. A long delivery tube 88 is extended downwards to the bottom of the mold, and the polymerizable mixture which will form the separating gel is dispensed. The motions of this tube and other delivery tubes are controlled by simple vertical electromechanical movements. In configuration B, after the separating gel 89 is polymerized, a second shorter delivery tube 90 is lowered and a stacking gel phase is dispensed. In configuration C, before the stacking gel 91 polymerizes, a slot form 92 is inserted into the mold to form the sample slot 93. In configuration D, once the stacking gel is polymerized, the slot form is withdrawn, an electrode rod 94 is inserted into the mold, and a third delivery tube 95 is lowered into the mold to dispense a top gel mixture. In configuration E, after the top gel 96 is polymerized, the mold is opened. Once the mold is opened, a completed slab gel 97 hanging from the electrode rod 94 is slowly and evenly removed by slab gel handling arm 98 having an actuated gripper 99. The arm is carried vertically and horizontally by linear motion components 100 and 101.

Figure 9K:
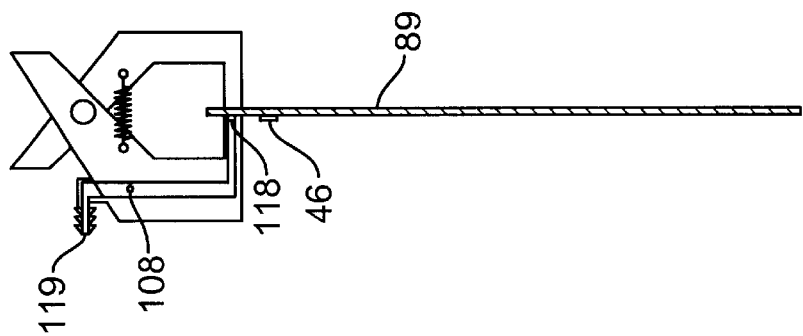
FIG. 9 illustrates alternative forms of slab gels.
Figure 9J:
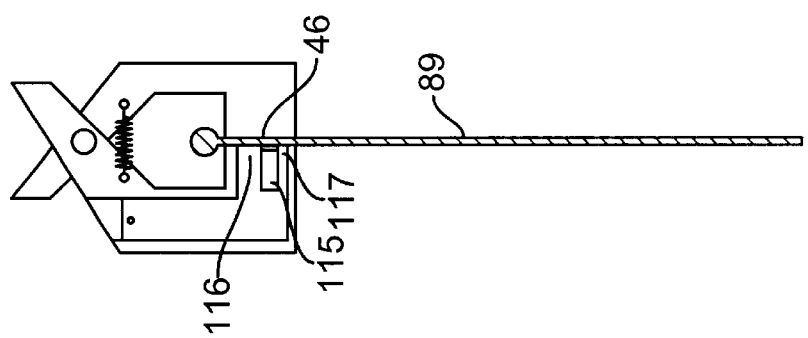
Figure 9I:
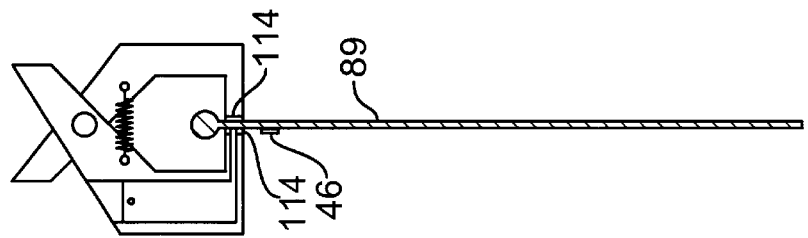
Figure 9H:
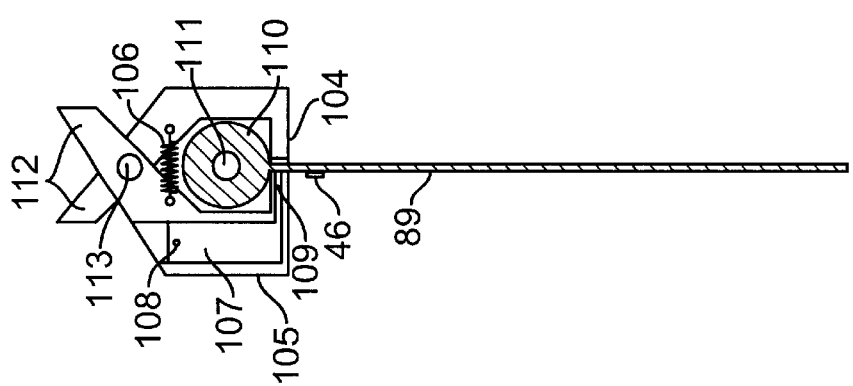

FIG. 9a illustrates alternative forms of slab gels. The preferred form of slab gel shown in configuration A comprises three gel phases (separating gel 89, stacking gel 91, and top gel 96), an internal slot-shaped cavity 93 to accommodate the IPG first dimension gel 46, and a rod-shaped electrode 94. In configuration B, the stacking gel phase is eliminated and the internal slot 93 is formed directly in the separating gel 89. In configuration C, the sample slot 93 extends to the top gel surface, while two internal electrode rods 94a and 94b are used. In configuration D, the sample slot 93 also extends to the upper surface, but the electrode rods 102a and 102b are external to the gel and support it by interacting with lips 103 on the gel's external surfaces. In configuration E, the IPG gel 46 is applied to an external face of the stacking gel phase rather than being placed in an internal slot, remaining in place as a result of surface tension. In configuration F, the IPG gel 46 is also applied externally, but to the separating gel 89 (the stacking gel 91 having been eliminated). In configuration G, the top phase 96 of a gel configured as in E is rotated counterclockwise by approximately 160 degrees. By rotating the incorporated electrode rod 94, the top gel phase 96 is brought in contact with the separating gel 89, bypassing the stacking gel 91 phase and the IPG gel 46, after sample proteins have entered into the separating phase.

A series of alternative embodiments make use of a gel clamp, instead of a distinct gel region, to provide an electrode and source of ions. In configuration H (FIG. 9b), a hinged clamp, comprised of halves 104 and 105, grasps the top edge of a slab gel and holds it as a result of the closing force exerted by spring 106. One of the two opposing faces 105) contains an internal cavity 107 and electrode 108, the cavity forming a liquid-tight vessel when the gel is clamped in place thereby covering opening 109. The gel is prevented from slipping out of the clamp by the presence of a region of increased gel thickness 110 along the top gel edge, in this case including a molded-in rod 111 as a means of handling the gel before introduction into the clamp, and secondarily by the presence of a gritty coating on one or both of the opposing faces of the clamp. Projections 112 above the clamp's axis 113 can be squeezed together to open the clamp and release the gel. Axis 113 is connected electrically to the liquid vessel's electrode. An IPG gel 46 is applied on the surface of the slab gel. Once the gel is grasped and the chamber 107 is filled with an appropriate volume of electrode buffer, the assembly can be grasped in turn by external means via axis 113, and manipulated by a robot arm as in the case of the gels with incorporated electrode rods (e.g., configuration A). The electrode buffer solution provides the source of ions for electrophoresis, using the axis 113 as a convenient external electrical contact.

In configuration I, a similar clamp is used to grasp a planar slab gel having no region of increased gel thickness along the top gel edge. The gel is prevented from slipping out of the clamp only by the grasping force and the presence of a gritty coating 114 on one or both opposing faces of the clamp. In configuration J, the IPG gel is placed within the clamp on a support structure 115, and thereby held against the slab gel. The buffer-containing internal cavity is formed to provide two paths of current flow 116 and 117 into the slab gel: one above and a smaller one below the IPG. This arrangement provides a means for directing the proteins transported from a surface-applied IPG during electrophoresis into the center plane of the slab gel. Hence, instead of moving along the surface of the slab to which they were applied (in the case where the IPG is applied to a surface, rather than inside of the slab), the protein zone is pushed towards the interior of the gel by the flow of buffer ions entering through the second path 117. In configuration K, the clamp contains a channel 118 through which buffer can be circulated. One leg of this channel 118 runs along the top edge of the slab gel, where one of the channel's walls is comprised of the gel's surface, and contains an electrode 108. This channel further communicates through additional passages 119 with an external buffer circulation system. In this embodiment, buffer is circulated through the clamp during the run, providing a supply of fresh buffer components which, with the electrode mounted in the channel, allow sustained electrophoresis with a minimum volume of reagents.

In the preferred embodiment, a separating gel (usually a gradient composition varying between approximately 18%T acrylamide at the bottom of the gel mold to 11%T acrylamide at the top of the separating gel phase) is introduced through the first delivery tube 88 (FIG. 8A) while it is extended to the bottom of the mold cavity. This gradient is produced by a second gradient maker similar in structure to that disclosed above to create an IPG gradient, except that larger syringes are used to produce a total separating gel volume of approximately 200 ml. After the gel is introduced, the first delivery tube 88 is raised out of the mold so that its open end lies in a block with vacuum channels that direct a stream of air across the end of the tube and thus aspirate emerging liquid into a waste container. Multiport valves associated with the gradient maker syringes are switched so that the syringes may be refilled, and so that a supply of pressurized water is connected with the manifold leading to the delivery tube, thus purging it of polymerizable components and flushing it with water. These techniques for providing and aspirating delivery wash solvent function in a manner similar to that described above for IPG gel formation. The separating gel is left undisturbed to polymerize for approximately 5 minutes.

After initial polymerization, a second gel phase, a stacking gel 91, is formed by extending the second delivery tube 90 into the top of the mold and dispensing approximately 50 ml of polymerizable stacking gel mixture directly atop the separating gel. The stacking gel 91 mix is formed by combining the output of three computer-controlled syringes delivering stacking gel mix, ammonium persulfate and TEMED. Before this gel phase polymerizes, the slot form 92 is caused to move down into the top of the slab gel mold. The slot form 92 consists of a thin strip 1 mm thick) of plastic mounted so as to present a vertical edge that lies on the mold center line which extends to within 1 cm of the separating gel top and within 1 mm of the diverging walls of the mold in the joining region. The slot form 92 is approximately 58 cm wide, leaving a 1 cm open space at either of its ends.

The stacking gel 91 volume is so contrived that the joining region is filled with stacking gel mixture up to a depth on the slot form of approximately 3 mm. Upon polymerization of the stacking gel 91, the slot form 92 thus creates a slot 3 mm deep in the horn-shaped stacking gel cross-section, into which an IPG gel 46 or other protein containing sample may be placed.

After polymerization of the stacking gel 91, the slot form 92 is withdrawn from the mold, and the arm system used for IPG manipulation is used to place an IPG strip in the slot so formed. Once this arm is again removed from the mold area, the second delivery tube 90 is once again introduced into the mold, and a volume of IPG equilibration solution is dispensed through it into the slot occupied by the IPG. This equilibration solution (consisting of 10% glycerol, 5 mM DTT, 2% SDS, 0.125M Tris HCl pH 6.8 and a trace of bromophenol blue) serves to infuse SDS into the IPG gel 46 and alter its pH to that of the stacking gel 91 in preparation for stacking. The second delivery tube 90 is then once again removed from the mold.

A second movable arm system then carries a carbon electrode rod 94 (or rods 99) to the mold and positions it within the mold, approximately 1 cm from the top of the mold cavity. The electrode rod ends rest in indentations at the ends of the mold cavity, maintaining the rod in position when released by the arm, which moves away from the mold after depositing the rod. The third delivery tube 95 is then introduced into the mold where it dispenses the third gel phase 96 (the top gel), filling the mold to the top. This top gel phase 96 is produced by a peristaltic pump system combining four components: an acrylamide/bis solution, a buffer solution, ammonium persulfate and TEMED.

The result is a slab gel in three phases, with the IPG first dimension gel 46 and a carbon electrode rod 94 polymerized inside. The polymerizable gel solutions for these three phases are designed to polymerize rapidly, so that the three phases adhere to one another and yield an integral gel whose regions have distinct electrochemical properties.

Preferred compositions for the three phases are as follows. Acrylaide™ (FMC Corporation) is an alternative gel crosslinker which may be used to increase gel strength in the stacking gel.

| Separating gel | | |
|---|---|---|
| Acrylamide | 13.00% | T |
| bis acrylamide | 3.8% | C |
| Tris HCl pH 8.6 | 0.375 | M |
| Stacking gel | | |
| Acrylamide | 8.00% | T |
| Tris HCl pH 7.0 | 0.375 | M |
| Acrylaide 2% | 3.2% | C |
| SDS | 0.2% | |
| Top electrode gel | | |
| Acrylamide | 13.00% | T |
| Tris base | 0.048 | M |
| Glycine | 0.4 | M |
| SDS | 0.20% | |

After the gel is made, the mold is opened by moving apart the mold halves 86 and 87 and leaving the gel on the movable, now nearly horizontal, mold half 87. A second computer-controlled arm system, equipped with two graspers or pincers 99 designed to engage the opposite ends of the electrode rod 94, is moved into position to seize the electrode rod 94 and then lift the gel upward and out of the mold. Gravity causes the gel to hang downwards from the bar.

Slab Gel Electrophoresis

Figure 10:
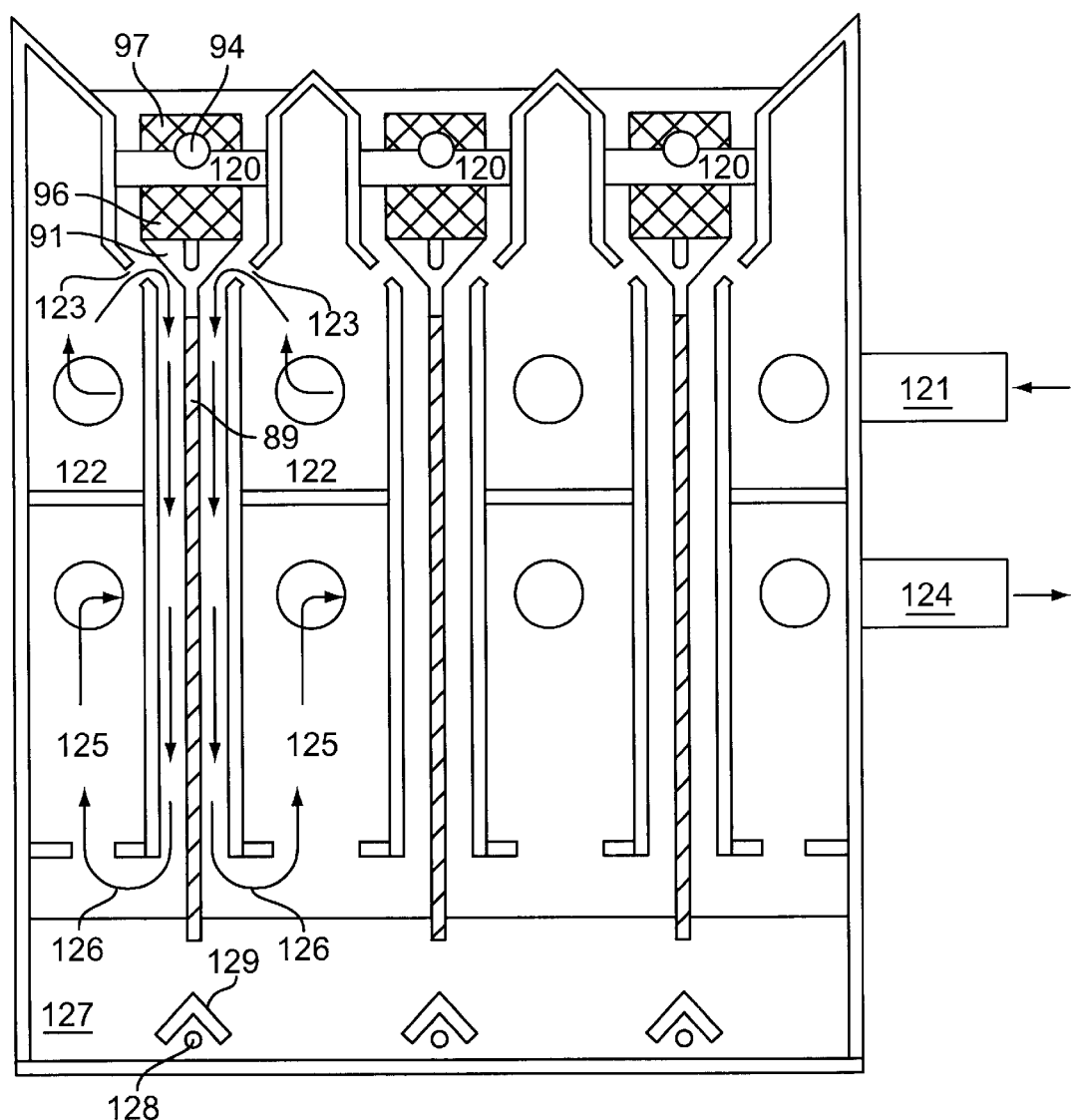
FIG. 10 is an end view of slab gel run tanks.

The arm is then moved laterally into position over an empty slot in a slab gel running tank and slowly lowers the slab gel into the slot. FIG. 10 illustrates a slab gel running tank in accordance with the present invention, wherein a slab gel 97 is suspended vertically in silicone oil during the second dimension electrophoresis run. The slab 97 is suspended by electrode rod 94 which rests on electrical bus bars 120 (one at either end of the gel), with the slab gel 97 inserted into a vertical slot through which cooled silicone oil is circulated. The oil circulation path is so contrived as to cause laminar flow of a curtain of oil downwards along both surfaces of the slab gel, thereby removing joule heat generated during electrophoresis. The oil is recovered at the bottom of the slots and recirculates through an external pump and heat exchanger, and thereafter is reintroduced into the top of the slot in a closed-loop system. This curtain-like flow of oil serves to prevent the slab gel 97 from touching the walls of the slot, and insulates it from electrical contact along its length. Oil enters the tank through manifold 121, is distributed to supply plenums 122, expelled through holes 123 into the gel slot, and flows down the slot on either side of the separating gel 89, to be sucked out through return manifold 124 via return plenums 125 and return holes 126.

At the bottom of the tank, below the level of the bottom of the slots, a lower electrically-conductive aqueous phase 127 (denser than the silicone oil) is positioned so that it just contacts the bottom edge of the slab gel 97. Current passes from the electrode bar or bars embedded in the top gel 96 through the stacking gel 91 and separating gel 89 to the lower aqueous phase and lower electrode 128, thus completing the circuit required for an electrophoretic separation. The shield 129 is provided over the lower electrode 128 to funnel the bubbles generated there to one side and up a separate pipe, thus preventing their rising through the aqueous phase and then the silicone oil phase, and causing mixing of the two phases.

At a voltage of 600 volts and a current of 1 amp, the separation of proteins in the separating gel 97 can be effected in approximately 4 to 5 hours. Once the separation is complete, the aforementioned slab gel arm system is used to grasp the ends of the electrode bar 94, raise the gel out of the running slot and move the gel into position over the first of several tanks containing solutions required to visualize the separated proteins by staining.

Slab gels and electrophoresis methods of the type disclosed can be used for separation of samples other than proteins contained in IPG gels. In particular, the inclusion of multiple sample wells in place of the single slot provided for an IPG allows use of such gels to separate protein or nucleic acid components of numerous liquid samples.

Slab Gel Staining

Several stain protocols can be executed including, among many others, staining with Coomassie Brilliant blue, ammoniacal silver, silver nitrate, and fluorescent stains such as SYPRO red and orange. The following example exemplifies the method applied to any stain. The gel is moved between subsequent tanks, by the arm under computer control, so that the precise time of movement from one solution to the next can be controlled, and can be held generally constant from gel to gel.

In a first tank, the gel is immersed up to the stacking gel in a solution of 30% ethanol, 2% phosphoric acid and 68% water for a period of two hours, to fix the proteins in place and remove most of the SDS, Tris and glycine in the gel. Following this fixation step, the gel is moved, through use of the arm, to a tank of 28% methanol, 14% ammonium sulfate, 2% phosphoric acid in water, where it is incubated for two hours. Next, the gel is moved to a tank of the same composition with the addition of powdered Coomassie Blue G250 dye, the whole liquid volume being continually circulated or agitated in the tank. Here the dye permeates the gel, binding to resolved protein spots. Finally, the gel is removed from this tank and transported by the arm to a scanning station.

Figure 11A:
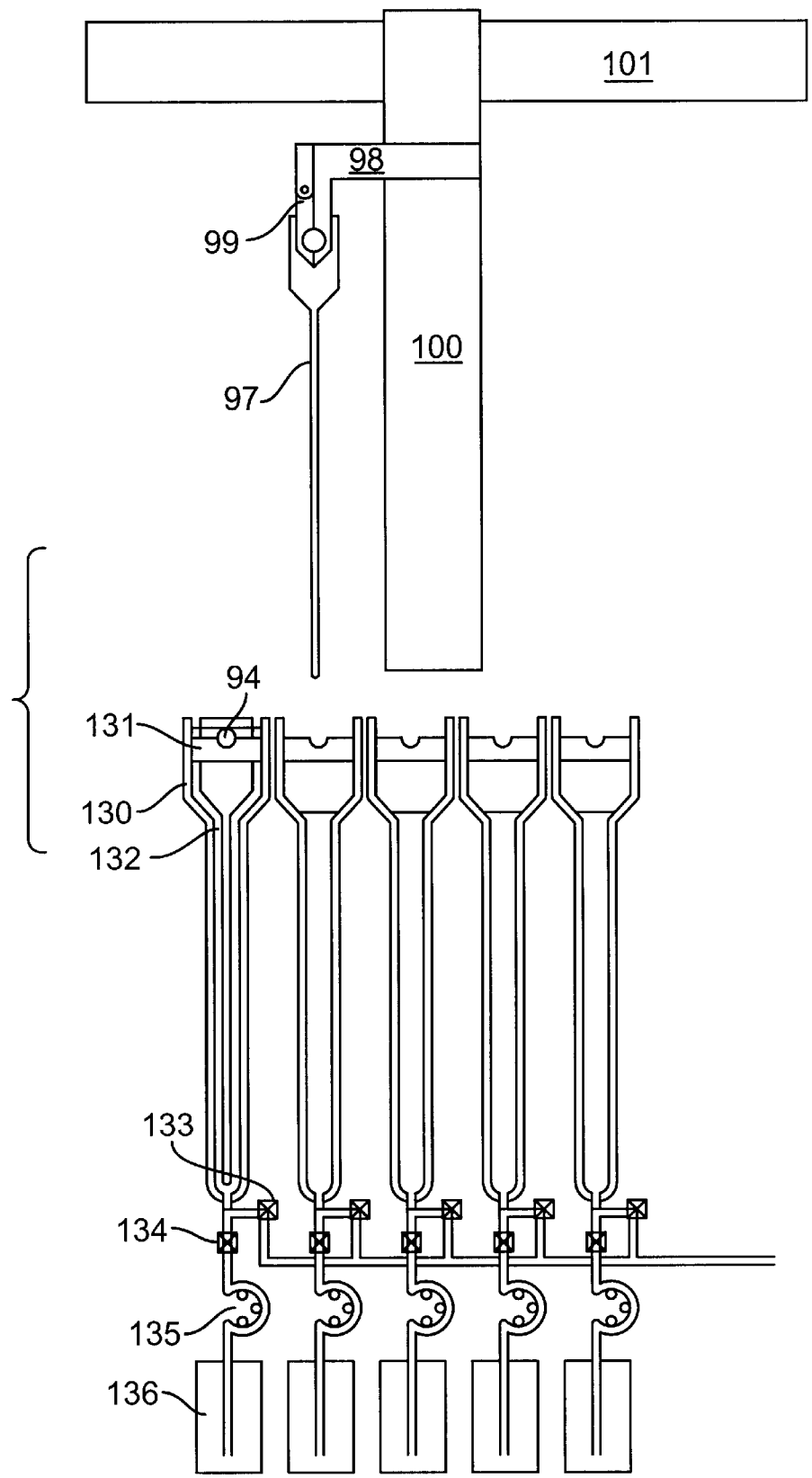
FIG. 11 is an end view of slab gel staining tanks with the slab carrier arm, and gel carriers.

FIG. 11A illustrates slab gel staining tanks with a slab carrier arm. In order to expose slab gels 97 to staining solutions, the gels are suspended in staining tanks 130, where they are supported by the embedded electrode rods 94 whose ends sit on projecting supports 131. The tank 130 is filled with stain solution 132, which can be removed from the tank by opening exit valve 133. The tank 130 can be refilled by closing valve 133 and then opening input valve 134 and activating pump 135 to deliver solution 132 from reservoir 136. Solutions in the tank can be agitated when required by a variety of means well known in the photographic processing industry, including bursts of inert gas (such as nitrogen or argon) introduced at the bottom of the tank, or by small mechanical motions of the suspended gels caused by cyclic movement of the gel supports 131. Gels 97 are moved from tank to tank by means of arm 98 having pneumatically controlled grippers 99 which seize the ends of electrode rod 94. The arm 98 is raised and lowered by vertical movement 100 which in turn rides on lateral movement 101, all under computer control.

Figure 11B:
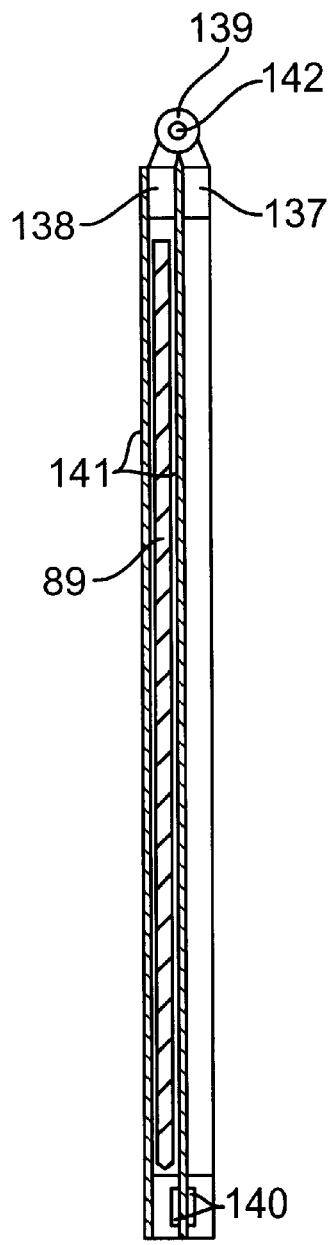
Figure 11C:
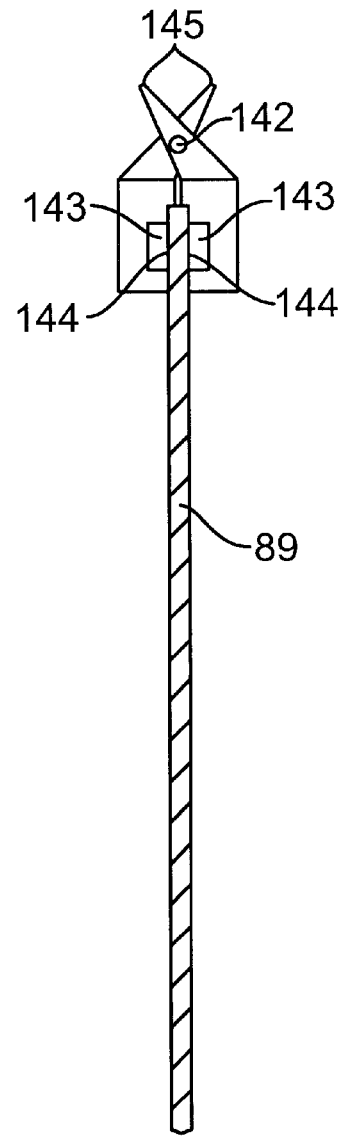

FIGS. 11B and 11C show alternative embodiments allowing gels without incorporated electrode rods to be similarly processed. In B, a slab gel 89 is contained inside a holder whose two halves 137 and 138 are connected by hinge 139 at the top edge and held together by magnets 140 at the bottom edge. Each half of the rectangular holder has a large cutout and is shaped like a picture frame. One surface of each half is covered with a taut mesh 141, resulting in a narrow gel cavity with large-area porous walls. A slab gel placed in such a holder is thus exposed to any solution into which the holder is immersed, and can be processed through a series of tanks using a robot arm to grasp projecting pins 142. In C, an alternative slab gel holder makes use of a clamp hinged at 142, held together by magnets 143 and having its internal faces 144 coated with a gritty coating, to grasp a slab gel for transportation and processing. Projections 145 may be squeezed together to open the clamp, releasing the gel.

Scanning

Figure 12:
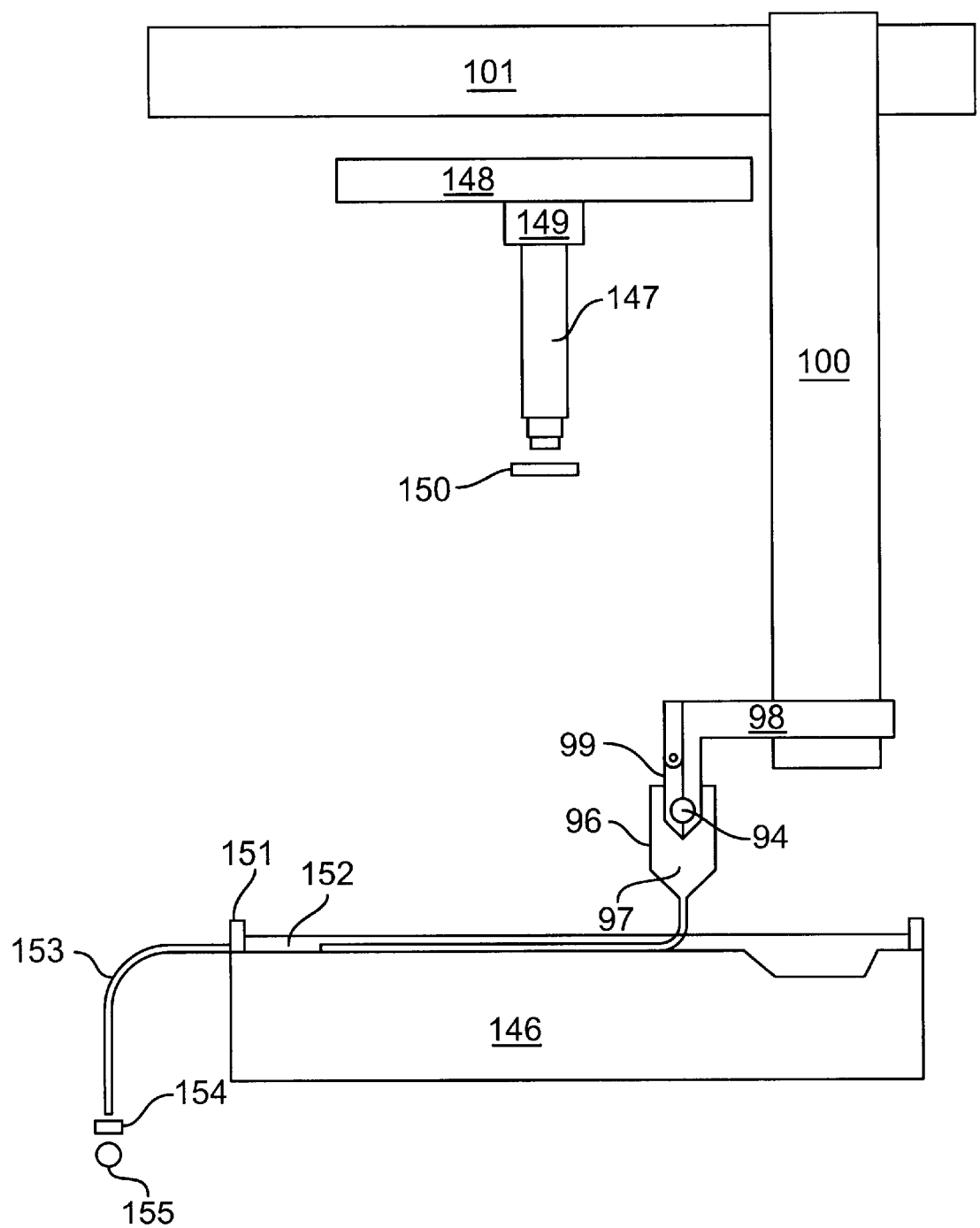
FIG. 12 illustrates the placement of a slab gel on a scanning platform by a slab carrier arm and configuration of fluorescence illumination.

In order to obtain quantitative data on the abundance of resolved proteins, the gel is scanned to yield a digitized image. FIG. 12 shows a gel 97 being gently laid down on a horizontal or tilted illuminating table 146 prior to scanning, grasped as before by the electrode rod 94 embedded in its top phase 96. To do this, the robotic arm 98 executes a coordinated vertical and horizontal motion so that the gel is laid down smoothly without tension. An overhead digital camera 147, such as a CCD digitizer, may then be used to acquire an image of the gel 97 and its stained protein spots in absorbance mode. In order to allow scanning of a large area gel at high resolution, a camera covering, for example, 1024×1024 pixels can be moved to a series of locations by orthogonal linear motions 148 and 149, generating a series of scans that can be combined to yield a larger image. Alternative scanning and illumination modes may be provided for measuring fluorescence or light scattering, in situations where the proteins have been stained with a fluorescent or a particulate dye, respectively. In the preferred embodiment, fluorescence excitation illumination is delivered to the gel in the plane of the gel while it lies in a horizontal cavity defined by walls 151 and filled with a liquid 152, such as water, having a refractive index similar to the gel. Light is piped into the cavity by an optical fiber light pipe 153, one of whose ends pierces the walls 151, the other end being illuminated by light produced by light source 155 filtered by interposed optical filter 154. In fluorescence mode, light emitted by fluorescent moieties in the gel is detected by the digitizer after passage through a second optical filter 150 which passes the dye's emission wavelength while blocking the excitation light. The approach described makes use of the fact that the exciting light is trapped by internal reflections in the gel/water plane, thus improving its availability to excite protein-bound fluorescent dye molecules and diminishing the amount of exciting light that escapes normal to the gel plane to impinge on the detector. A similar optical system, but without a requirement for excitation and emission filters, can be used to detect light scattering by particles generated either on the protein spots (for example by the silver stain) or around the spots (leaving the proteins negatively stained, as occurs with the copper stain).

Using the automated staining system described, multiple stain and scan cycles can be sequentially applied to the same gel. By staining first with a relatively low sensitivity stain such as Coomassie Blue and scanning, and then staining with a relatively sensitive stain such as the silver stain and scanning once again, it is possible to obtain quantitative protein abundance measurement over a wider dynamic range than can be afforded by any single conventional stain.

Multiple sequential scans of the same gel may be used to increase the precision and dynamic range of non-equilibrium stains such as the silver stain. In such stains, the development process reveals first the intensely staining spots (in general the more abundant proteins), then those of moderate staining intensity, and finally those of low staining intensity (typically low abundance proteins), at which point the intensely staining spots are over stained, being saturated in stain absorbance and appearing increased in size. By scanning the gel two or more times during development, quantitation of spots can be based on measurements of parameters other than simple optical density. The most useful of such parameters include maximum rate of change of absorbance (effectively the maximum slope observed in a plot of optical density versus time) and time of onset of development (the time after the beginning of development at which a given increment of optical density is observed), both of which can be calculated for each pixel in the scanned gel image through use of multiple scans yielding optical density (or transmittance) as a function of time during the development of the gel. Alternatively, sophisticated curve-fitting algorithms can be used to devise functions of absorbance as a function of time that yield, for each pixel, a derived parameter well correlated with known differences in abundance.

Multiple scans of the same gel can also be used to compare protein samples, provided that the proteins of each sample are labeled prior to electrophoresis with a dye or other substituent that can be detected separately from other such labels. Multiple samples labeled with a series of different fluorescent dyes having distinct emission wavelengths, for example, can be mixed and co-electrophoresed. By using appropriate optical filters to detect these dyes (and thus the proteins to which they are bound) separately, the protein content of each sample can be measured separately from the protein contents of other samples applied to the same gel. When used in a 2-D procedure that includes isoelectric focusing, such labels must be attached to the protein in such a way that the protein's net pI is unaffected: if, for example, the label is attached by reaction with a lysine primary amino group, then the label must have a net charge of +1 to compensate for the single positive charge of the primary amino group lost when the lysine is derivatized. While this approach increases the information output of each separation (by multplexing samples), it also makes possible a substantial increase in net resolution available for the comparison of samples. This comes about because the different label distributions observed in a small gel region (a protein spot in a 2-D electrophoresis pattern) can be compared with great sensitivity by mathematical techniques to determine whether the shape and location of a spot in one label channel is precisely the same as the shape and location of a spot in another label channel (both labels being detected on the same gel where they reveal the proteins of two different samples). Spot positional differences detectable by this approach (using for example a correlation coefficient to determine whether the spot profiles in two channels are the same or different) can be on the order of 0.1 mm, far less than the 0.5–2.0 mm position difference typically required to characterize protein spots as being different when two different gels are compared, or when two samples are co-electrophoresed on one gel and stained with a single stain. When applied to both dimensions of a 2-D procedure, this method of comparing potentially co-electrophoresing proteins can result in an effective 100-fold increase in net gel resolution (the product of an approximate 10-fold resolution increase in each dimension). Such an approach is of particular value in comparing very different protein patterns (for example different tissues), where it is likely that different proteins with similar 2-D gel positions may be encountered.

Spot Excision

Figure 13:
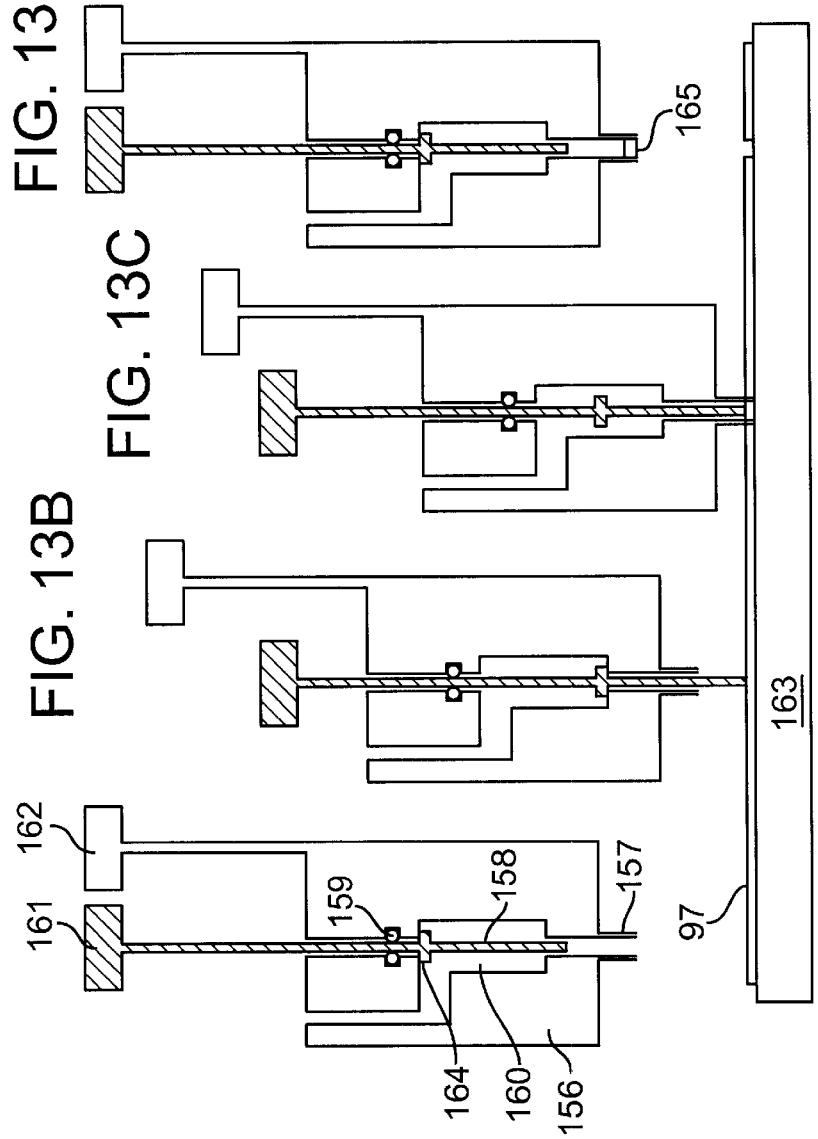
FIG. 13 illustrates the sequence of actions of a spot excision punch.

Protein spots can be excised from the gel under computer control once their positions are established by the aforementioned scanning. FIG. 13 shows a mechanical cutter comprised of a block 156 in whose lower part a thin-wall tube 157 is mounted vertically to act as a spot-cutting punch. The block and all its components are mounted on a movable, computer controlled X-Y frame, suspended just above and co-planar with the gel, such that the cutter 157 can be positioned over any spot to be excised from the gel. A plunger 158 is arranged so as to moved vertically within the punch. The plunger extends through a hollow cavity 160 in the block and exits through a second hole by means of channel containing an O-ring seal 159. The plunger is moved vertically by an actuator 161, and the block is moved vertically by a second actuator 162 having less force, and thus capable of being overridden by actuation of the plunger actuator. The gel to be cut 97 lies horizontally on a flat plat 163, which can be identical to the scanning platform/lightbox 146. In operation, the cutter performs a series of steps as shown in the figure. In configuration A, the block is positioned over the spot to be cut. In configuration B, the plunger actuator is pressed down, forcing the plunger to protrude through the cutting tube 157 into close proximity with the gel surface and further forcing the block partially down through interaction of collar 164 on the plunger with the block. In configuration C, actuator 162 is forced down, forcing the cutter through the gel and into contact with the supporting plate 163. In configuration D, the plunger actuator 161 is pulled upwards, moving the block up by interaction of collar 164 with the block and simultaneously generating suction in the cutter tube so as to ensure that the cut gel plug 165 is lifted away from the gel by the upwards motion. In configuration E, the cutter has been repositioned over a collection vessel 166, and the plunger forced down to expel the gel plug into the vessel. In configuration F, with both actuators in the up position, a stream of wash liquid is introduced through hole 167 in the block 156 so as to expel any contaminating particulate gel material remaining in the punch into a waste receptacle 168. Under computer control, the spot cutting mechanism can excise hundreds of spots from a single 2-D protein separation, depositing them in 96-well plates or other vessels for subsequent analysis by other means such as mass spectrometry. In the preferred embodiment, the spot cutter mechanism is incorporated into the gel scanning system, thus allowing the gel to be cut in an automated fashion immediately following computer analysis of the gel image obtained from the scanner.

System Scheduling Algorithms

Operating as a continuous production line, the automated 2-D gel system described must allow flexible scheduling of each component action in the multi-step process required to make and run each gel. If every gel were run using the same protocol, it would be possible to design a completely synchronous scheduling system in which each action recurred at precisely defined intervals. However, such a system is inherently inflexible and would not allow running successive gels with different parameters (e.g., different IPG pH gradient, focusing volt-hours, or time in a stain solution). In addition, any temporary halt required in such a synchronous system, due for example to an equipment breakdown, would cause variable and unforeseen consequences at different stages of the process.

Hence in the preferred embodiment, a non-synchronous scheduling algorithm is used in which a series of steps is laid out for the first sample to be run, and these are entered into a database of actions required, each step associated with a relative or absolute time at which it should be executed. Then a second series of steps is laid out for the second sample to be run, and these are entered into the database including a start delay calculated so as to prevent any action required for the second gel from being interfered with by any action required for the preceding (first) gel. Additional gels are added in order by the same procedure, ensuring in each case that the actions required for a gel do not interfere with those required for previously entered gels. Actions to be entered include casting an IPG gel, transporting an IPG from the caster to a wash slot, transporting an IPG from a wash to a drying slot, casting a slab gel, moving a slab gel from mold to running slot, moving a slab gel from a running slot to a stain slot, etc. Database entries take account of the time required to execute such actions, e.g., the time to move a gel from one station to another or to empty and refill a stain tank. The sequence of operations required to effect the processing of a series of gels, including interleaving of actions on different gels, is readily obtained by retrieving from the database a series of steps sorted by time of scheduled execution. Making use of the ability of database software to sustain multiple independent queries, different software modules controlling specific parts of the hardware system may retrieve a subset of actions (in scheduled time order) appropriate to them.

The automated system is then operated under the control of one or more computer programs which function by examining the database of scheduled actions, selecting from the database those actions appropriate to the hardware components being controlled by that program, and executing them at the time specified in the appropriate database record. Hence, a single IPG manipulation arm will be caused to transport IPG gels at different stages of the process between the required slots and stations, actions on different gels thus being interleaved in a flexible manner. Since each gel is separately scheduled at the outset, it can have a different protocol or different parameters than the preceding or succeeding gel, without limitation.

Data Reduction

Scanned images of 2D protein patterns are subjected to an automated image analysis procedure using a batch process computer software (e.g., Kepler® software system). This software subtracts image background, detects and quantitates spots, and matches spot patterns to master 2D patterns to establish spot identities. The final data for a 2-D gel, a series of records describing position and abundance for each spot, are then inserted as records in a computerized relational database.

Other Uses and Embodiments

The methods disclosed herein can be used for a series of alternative analytical applications including the analysis of DNA and RNA, as well as peptides. Either the automated IPG or slab gel system can be used for high-throughput one-dimensional analyses of relevant biomolecules as well as for 2-D.

Spot Cutter

Figure 14:
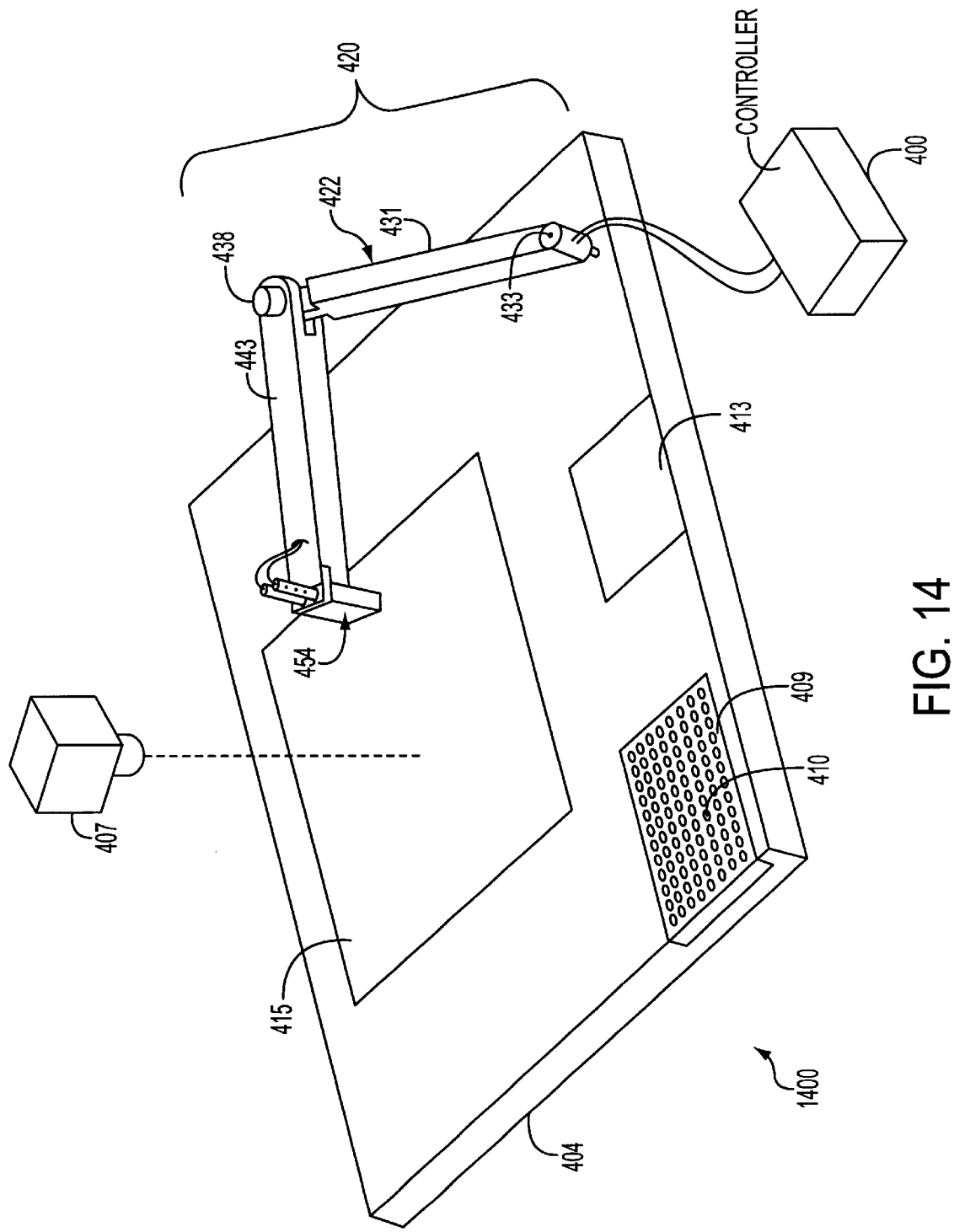
FIG. 14 shows a first embodiment of a spot cutter, including a controller, a support table, an image detector, and a spot cutter mechanism.

FIG. 14 shows a first embodiment of a spot cutter 1400, including a controller 400, a support table 404, an image detector 407, and a spot cutter mechanism 420.

The spot cutter mechanism 420 comprises a positioning mechanism 422 and a spot cutter head 454 affixed to the positioning mechanism 422. The positioning mechanism 422 is directed by the controller 400 and enables the spot cutter head 454 to be moved over a working region of the support table 404 (i.e., a region accessible to the spot cutter head 454). The controller 400 may therefore position the spot cutter head 454 over an electrophoresis gel positioned on the support table 404 (see FIG. 15), and may activate the spot cutter head 454 in order to excise an electrophoresis gel region. The excised electrophoresis gel region may be retained, recorded, and later used for analysis of macromolecular components.

The electrophoresis gel 500 of the present invention is free and unsupported and lies on the transparent plate 415 with very little to hold it in place. It therefore has a very limited spatial stability. The unsupported electrophoresis gel 500 of the present invention may be picked up, carried and processed without having any sort of supporting substrate whatsoever. There is no bond to be broken between the electrophoresis gel 500 and an underlying support surface. Therefore, the cutting operation is simpler and less likely to damage the unsupported electrophoresis gel 500, as the spot cutter of the invention does not have to additionally move a cutting tip in the plane of the gel during the cutting process.

The capability of the spot cutter to excise a spot in an unsupported electrophoresis gel 500 lies in the ability of the device to transport and yet retain the electrophoresis gel 500 without having to bond the electrophoresis gel 500 to a substrate or support. In the present invention, this may be accomplished by a gel retaining device. The gel retaining device may be one or more rough textured regions of the transparent plate 415, ferromagnetic regions and magnets, or a clamp or clamps.

The support table includes a working region, a transparent plate 415 comprising at least part of the working region, a sample well 409, and a rinse well 413. The transparent plate 415 is preferably a glass plate, but other materials may also be used, such as a transparent or translucent plastic. An electrophoresis gel may be positioned in the working region over the transparent plate 415 in order to support the electrophoresis gel for excision of spots or other regions of interest.

The sample well 409 may include a plurality of holes 410 in which are deposited excised electrophoresis gel portions. For example, each hole 410 may contain one excised electrophoresis gel portion, with the original location in the gel and the location of the, hole 410 in the sample well 409 being recorded by the controller 400. In this manner, the controller 400 may create a record that correlates individual excised electrophoresis gel portions to their original location in a gel. The record may be used for later analysis of the macromolecules contained within the excised electrophoresis gel portions. The sample well 409 may be a commercially available 96 well plate known in the art.

The rinse well 413 may contain some manner of rinse fluid such as, for example, water. The spot cutter head 454 may pause over the rinse well 413 between excising operations and expel a fluid, such as water, for example, in order to remove any electrophoresis gel portions or residues from the spot cutter head 454. The expulsion of fluid may be done simply by opening a valve, allowing the fluid to flow under the influence of gravity, or may be done by forcing the fluid under pressure through the spot cutter head 454. The expulsion is typically done after an excised electrophoresis gel portion is deposited in a sample well. Alternatively, before or after each excision, the controller 400 may dip the cutting portion of the spot cutter head 454 into the rinse well 413 in order to remove residue and prevent contamination or to aid in the excision process.

The image detector 407 may be positioned above the transparent plate 415 and may capture an image of an electrophoresis gel positioned on the transparent plate 415. The image detector 407 may be used to scan and detect spots (spots of macromolecular concentration due to the electrophoresis process) for excision. The image detector 407 may be a camera, a digital camera, or a charge-coupled device (CCD), for example. The controller 400 may use the image to locate and excise electrophoresis gel regions. Also in the preferred embodiment, a light source (not shown) may be positioned below the transparent plate 415 in order to enable a better image capture by the image detector 407.

The spot cutter mechanism 420 in this first embodiment comprises a robotic arm 422. The robotic arm 422 positions the spot cutter head 454 in a desired location, with the spot cutter head 454 being maintained at a substantially constant height above the support table 404.

The robotic arm 422 includes a first robotic arm segment 431 and a second robotic arm segment 443. The spot cutter head 454 is attached to the second robotic arm segment 443. The second robotic arm segment 443 is pivotally attached to the first robotic arm segment 431 by a first pivot drive mechanism 438. This first pivot drive mechanism 438 may be, for example, an electric stepper motor, an electric servo motor and an associated rotary or linear encoder or other positional feedback device, a pneumatic drive such as, for example, a pneumatic cylinder or motor, or a hydraulic drive such as, for example, a hydraulic cylinder or motor. The second robotic arm segment 443 pivots in a substantially horizontal plane.

The first robotic arm segment 431 is rotatably attached to a support structure such as, for example, the support table 404. Alternatively, the first robotic arm segment 431 may be attached to a structure adjacent to the support table 404. The first robotic arm segment 431 may rotate in a horizontal plane. The first robotic arm segment 431 includes a rotation mechanism 433 that is under control of the controller 400. The rotation mechanism 433 may be, for example, an electric stepper motor, an electric servo motor, a pneumatic drive, a hydraulic drive, a worm gear drive, etc.

Figure 15:
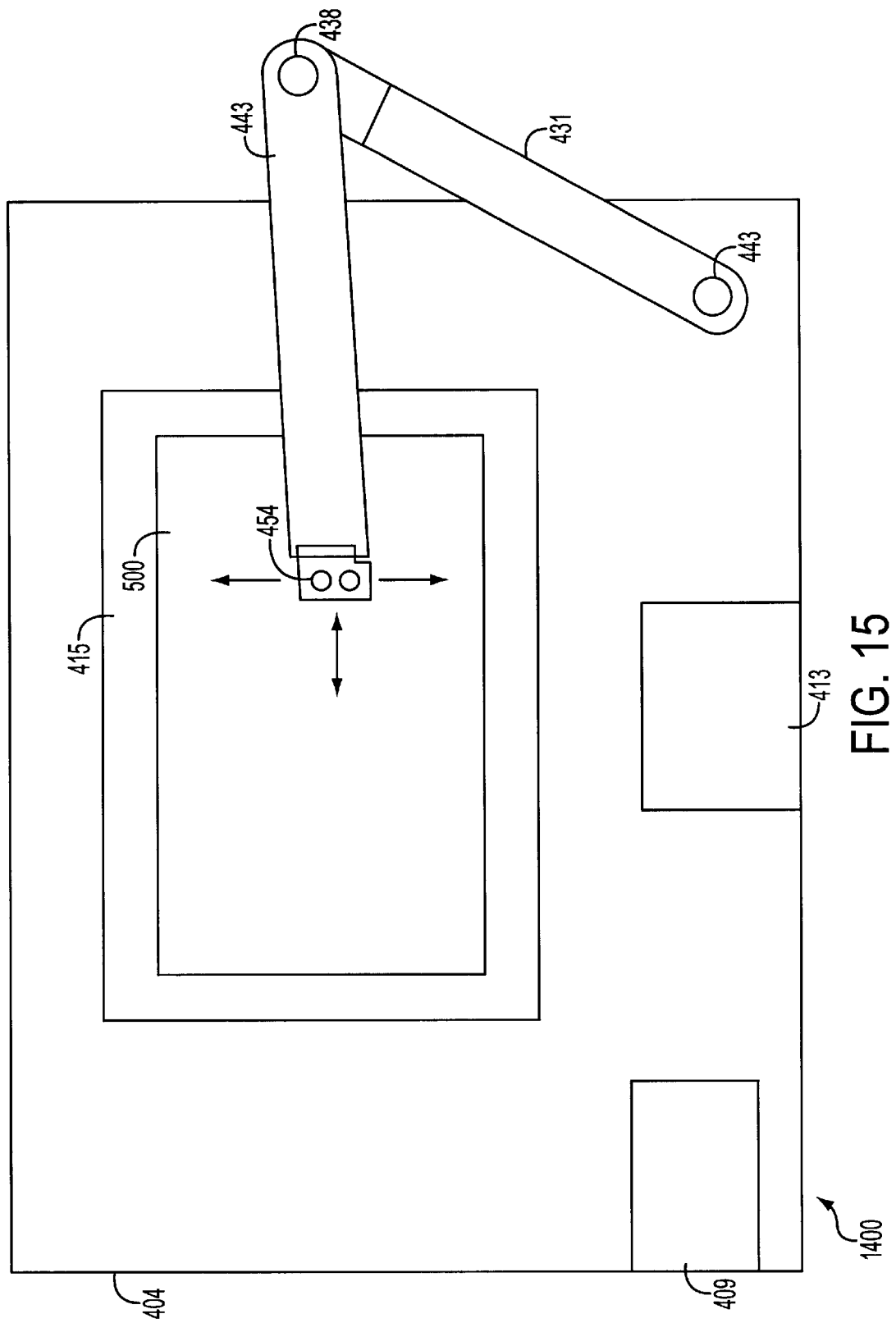
FIG. 15 shows an overhead view of the first embodiment illustrating motion of the spot cutter head.

FIG. 15 shows an overhead view of the first embodiment 1400 illustrating motion of the spot cutter head 454. This motion may be utilized in order to cover or excise spots within the electrophoresis gel 500 located on the transparent plate 415. The spot cutter head 454 may be moved by the robotic arm 422 to reach most areas of the support table 404, including the sample well 409 and the rinse well 413.

Figure 16:
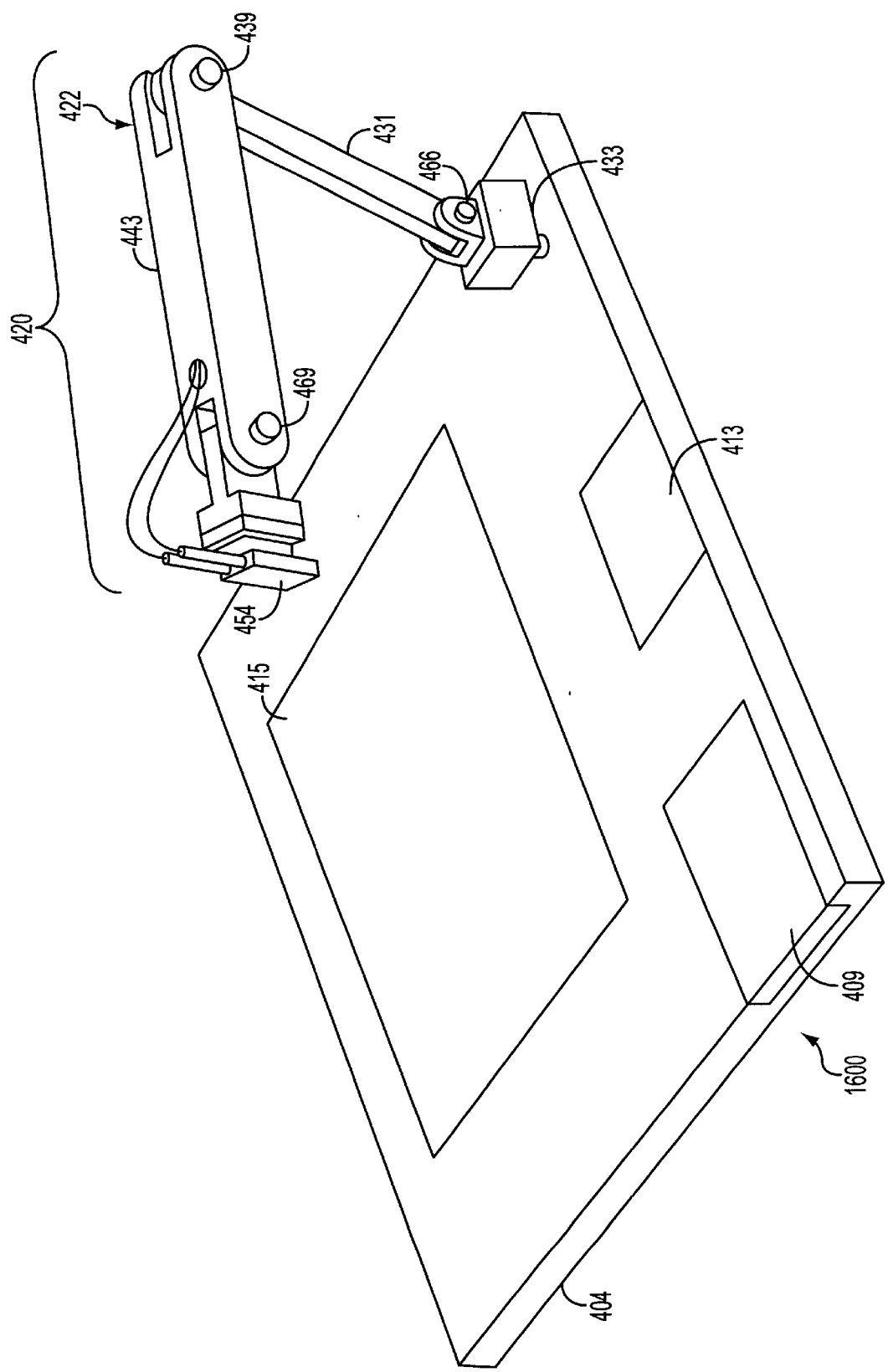
FIG. 16 shows a second embodiment of the spot cutter mechanism.

FIG. 16 shows a second embodiment 1600 of the spot cutter mechanism 420. In the second embodiment 1600, the first robotic arm segment 431 is pivotally attached to the second robotic arm segment 443 by a second pivot drive mechanism 439 that pivots the second robotic arm 443 in a vertical plane. The spot cutter head 454 is pivotally attached to the second robotic arm 443 by a spot cutter head pivot drive 469 that also pivots in a substantially vertical plane.

As in the first embodiment 1400, the first robotic arm segment 431 of the second embodiment 1600 is rotatably attached to the support table 404 or other support structure by a rotation mechanism 433. In addition, the first robotic arm segment 431 is attached to the rotation mechanism 433 by a first pivot drive mechanism 466 that pivots in a substantially vertical plane.

By using all three pivot points and the point of rotation, the robotic arm 422 may move the spot cutter head 454 to locations above the support table 404. In addition, the robotic arm 422 of the second embodiment 1600 may move the spot cutter mechanism vertically in relation to the support table 404.

As in the first embodiment, the various pivot drive mechanisms and rotation mechanisms may include electric stepper motors, electric servo motors, pneumatic drives, hydraulic drives, or other actuators.

Figure 17:
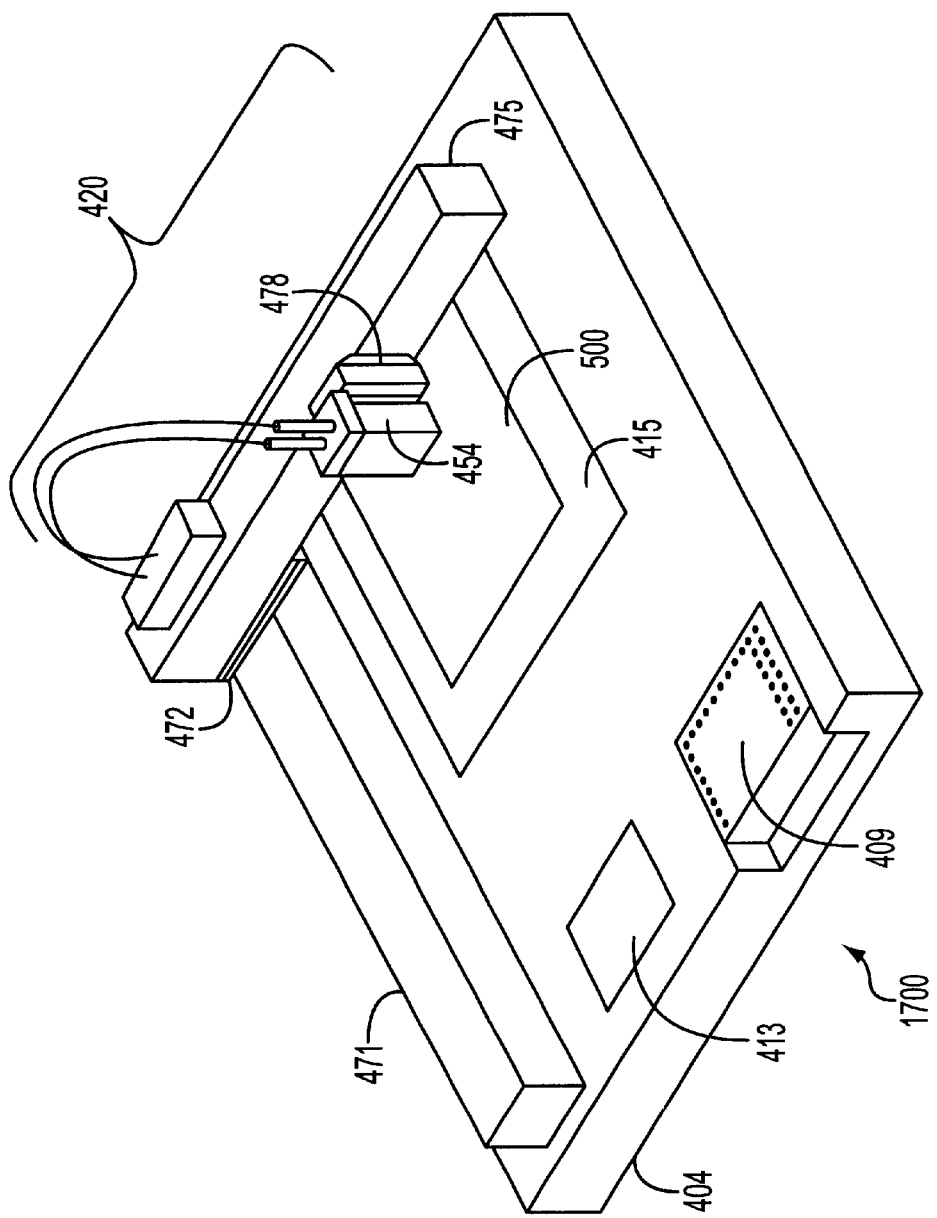
FIG. 17 shows a third embodiment of the spot cutter mechanism.

FIG. 17 shows a third embodiment 1700 of the spot cutter mechanism 420. In the third embodiment 1700, a rail 471 is positioned on the support table 404 and an arm 475 moves on the rail 471. The arm 475 is substantially orthogonal to the rail 471. The arm is moved by a first drive mechanism 472. This first drive mechanism 472 may be, for example, an electric stepper motor, a pneumatic or hydraulic drive, a worm gear drive, or a mechanical linkage, such as a chain, cable or wire drive.

The spot cutter head 454 is movably attached to the arm 475 and is moved by a second drive mechanism 478. The second drive mechanism 478 may likewise be an electric stepper motor, a pneumatic or hydraulic drive, a worm gear drive, or a mechanical linkage, such as a chain, cable or wire drive. Therefore, the spot cutter head 454 may be moved and positioned over a large region of the support table 404, including over the sample well 409 and over the rinse well 413, in addition to locations above the transparent plate 415.

As in the previous two embodiments, the first drive mechanism 472, second drive mechanism 478, and the spot cutter head 454 are under control of the controller 400.

Figure 18:
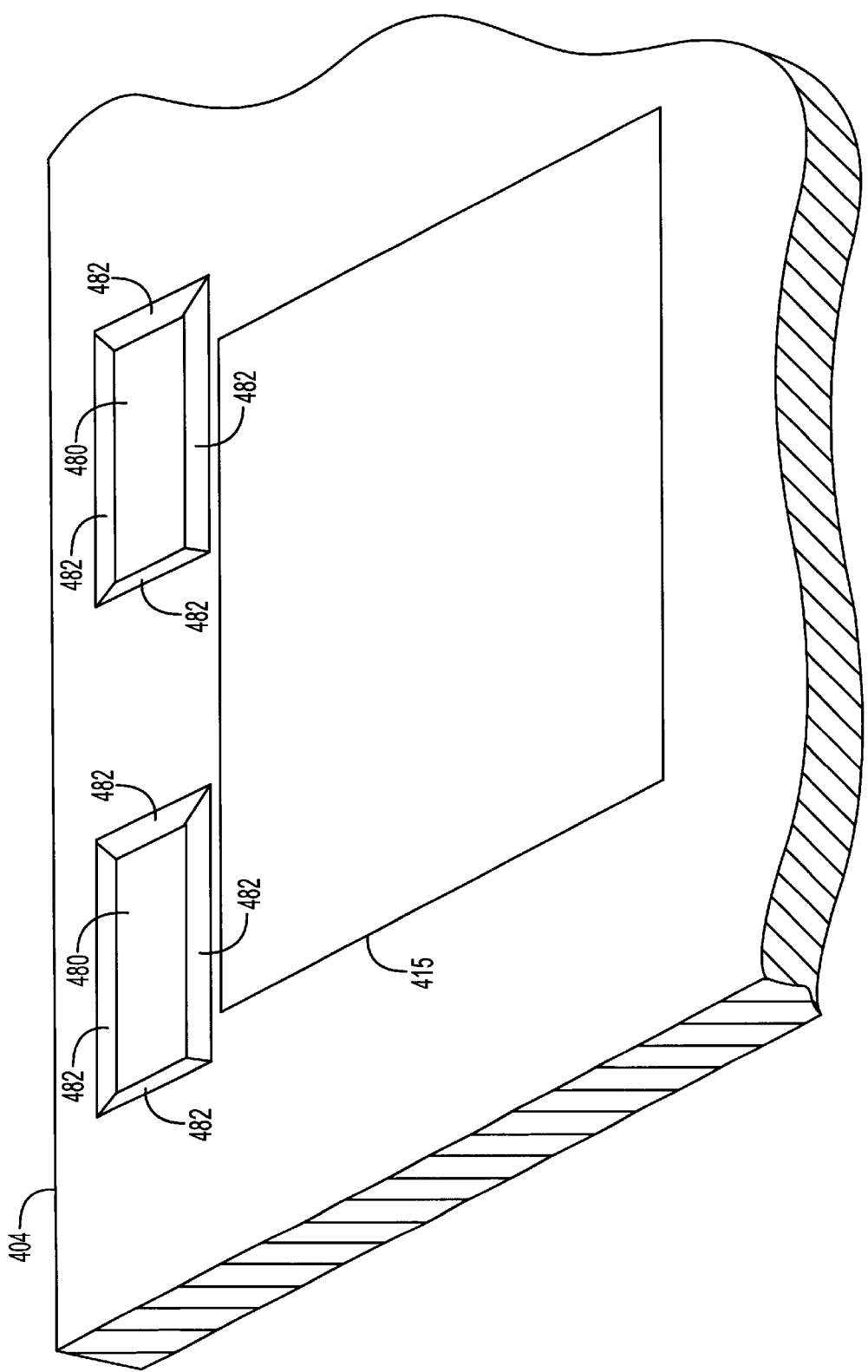
FIG. 18 shows additional detail of the support table wherein one or more depressions are formed in the surface of the support table adjacent to the transparent plate.

FIG. 18 shows additional detail of the support table 404 wherein one or more depressions 480 are formed in the surface of the support table 404 adjacent to the transparent plate 415. A depression 480 may include a beveled edge or edges 482. A depressions 480 may accommodate a transport device that transports and positions the gel and electrophoresis gel 500 on the support table 404. This is shown below in FIG. 19.

Figure 19:
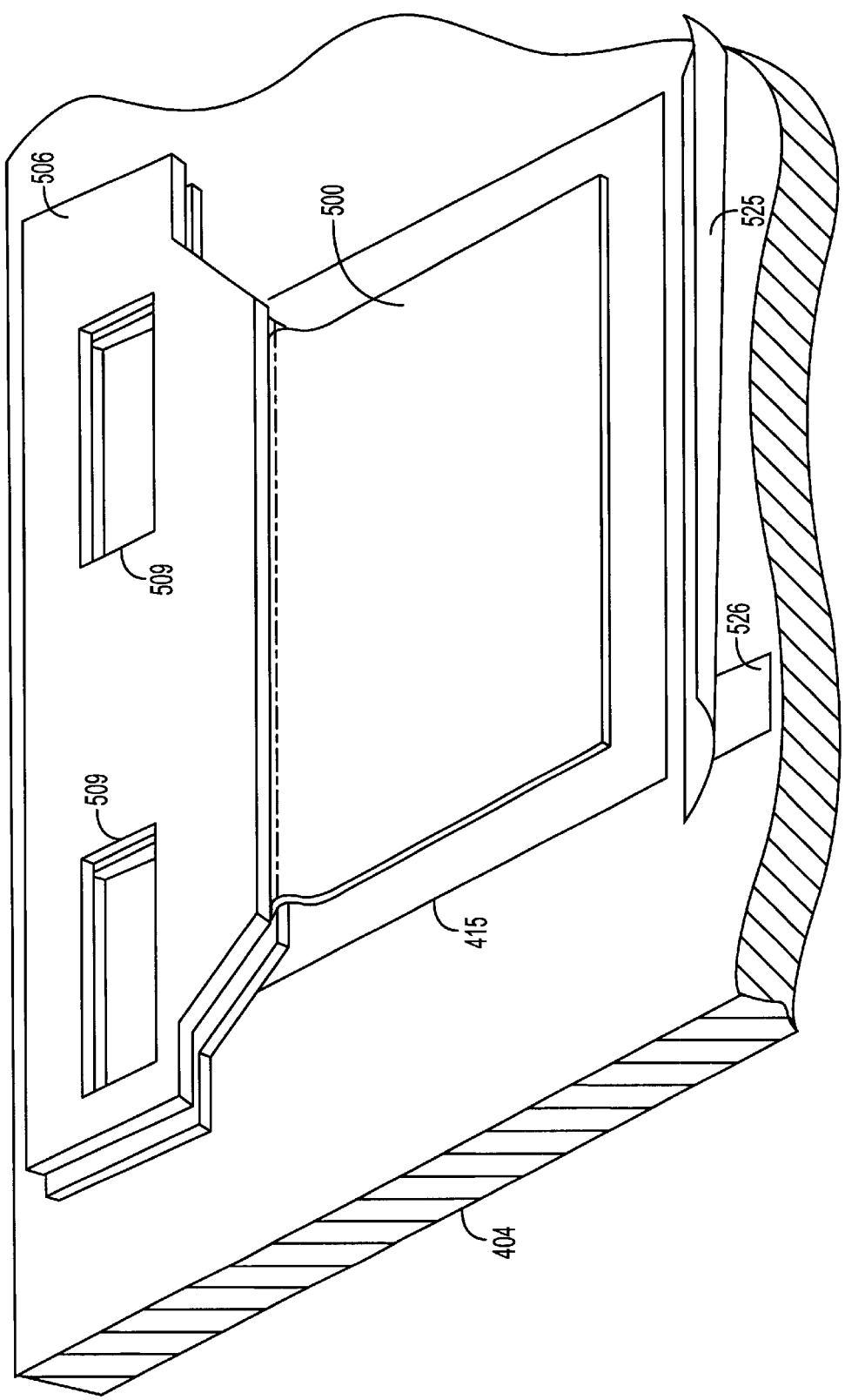
FIG. 19 shows an electrophoresis gel in position on a support table including two depressions.

FIG. 19 shows an electrophoresis gel 500 in position on a support table 404 that includes two depressions 480. At least one clamp 506 is used to removably attach to the electrophoresis gel 500 in order to transport and position the gel. The clamp 506 may be located anywhere around the periphery of the transparent plate 415, or alternatively anywhere on the support table 404 where the clamp 506 may engage an edge of the electrophoresis gel 500. The clamp 506 includes holes 509 through which handling projections or fingers (not shown) lift and grasp the clamp and, therefore, the electrophoresis gel 500. The clamp 506 is therefore used to position the electrophoresis gel 500 over the transparent plate 415. The depressions 480 allow the handling projections to pass through the clamp 506 in order to grasp and manipulate the clamp. Note that multiple clamps 506 may be used to retain the electrophoresis gel 500.

Also shown in this figure is a pivoting plate 525 that is pivotally attached to the support table 404. The pivoting plate 525 may be pivoted into place on top of a portion of the electrophoresis gel 500 in order to additionally hold or apply a force to the electrophoresis gel 500.

Figure 20:
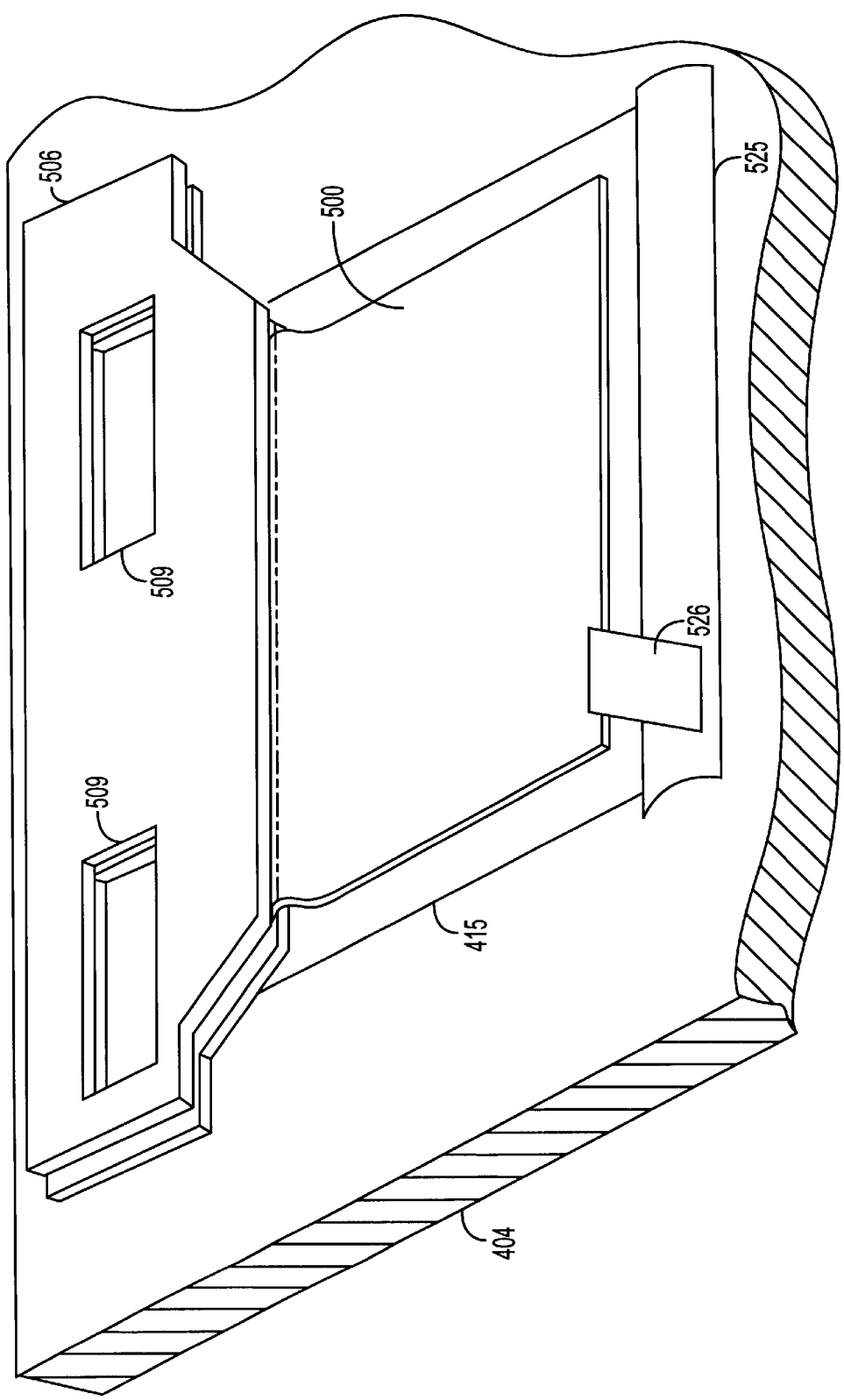
FIG. 20 shows the pivoting plate in a holding position down on and in contact with the electrophoresis gel.

FIG. 20 shows the pivoting plate 525 in a holding position down on and in contact with the electrophoresis gel 500. The pivoting plate 525 also includes a projection 526 that may be used to disengage the pivoting plate 525 when the electrophoresis gel 500 is to be removed from the support table 404. The projection 526 may be contacted and depressed, such as by an associated transport mechanism, in order to pivot the pivoting plate 525 back up and away from the electrophoresis gel 500 (as shown in FIG. 19).

Figure 21:
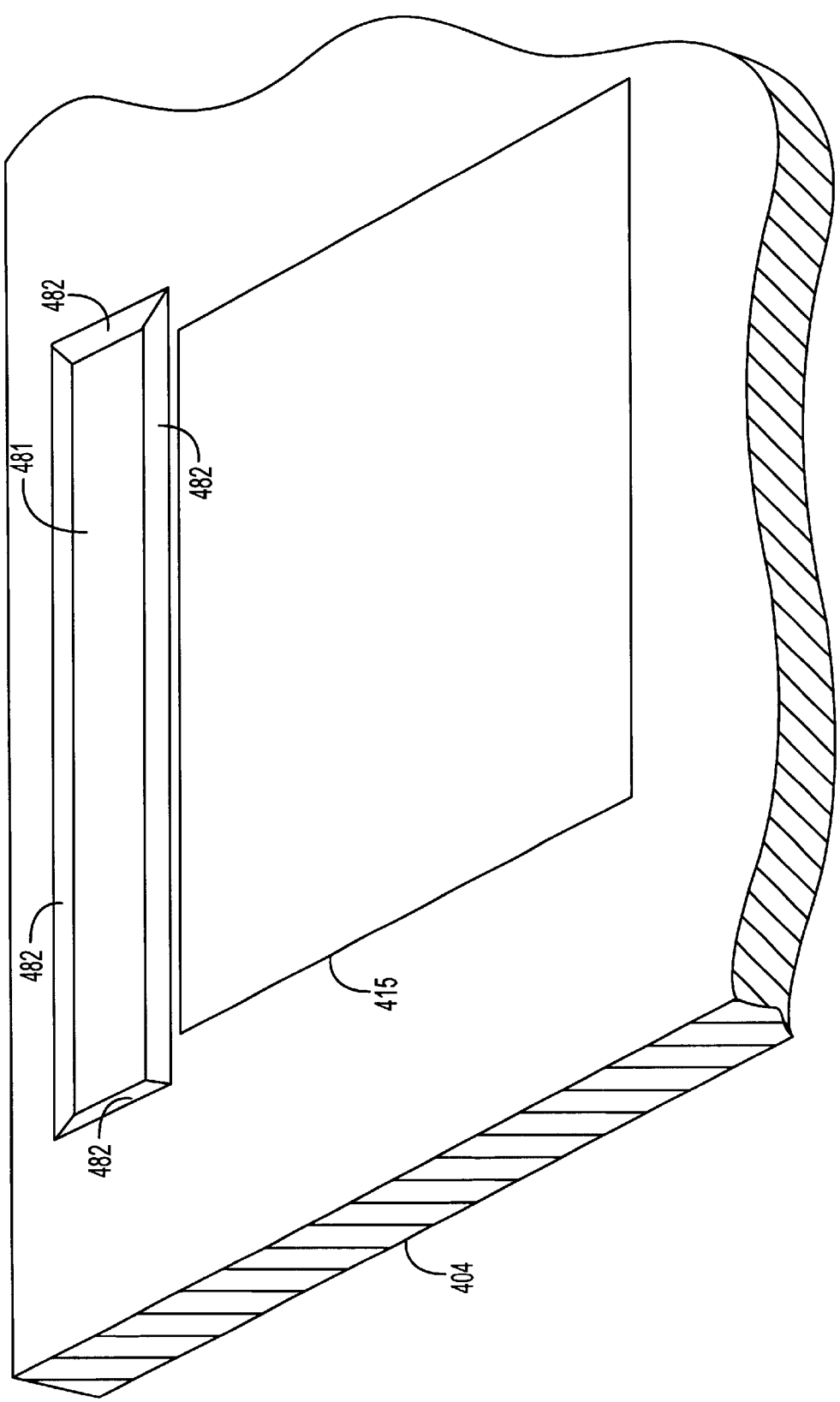
FIG. 21 shows another embodiment of the support table including a single depression.

FIG. 21 shows another embodiment of the support table 404 wherein a single depression 481 is formed adjacent to the transparent plate 415.

Figure 22:
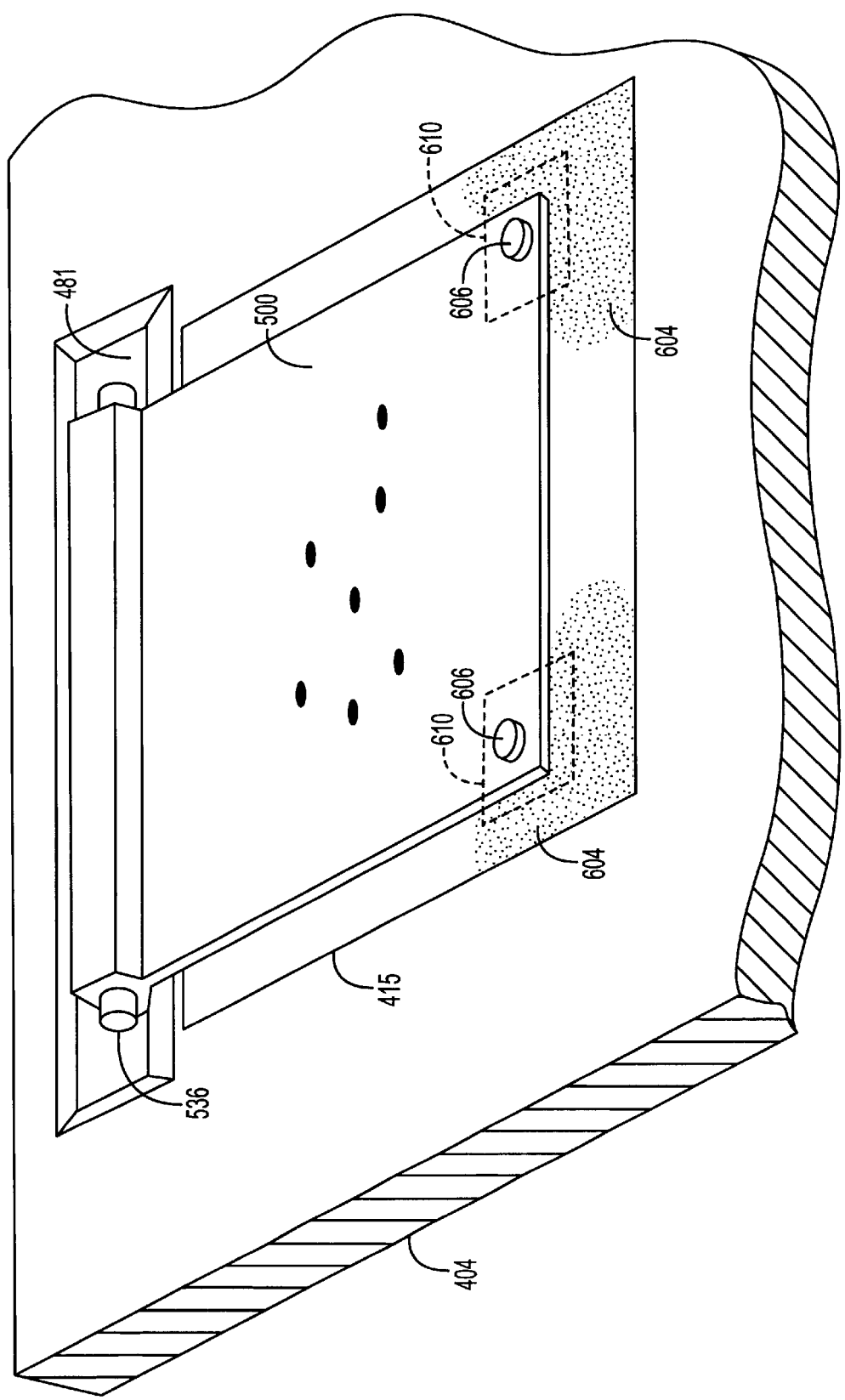
FIG. 22 shows the support table embodiment of FIG. 21 where the depression is used to receive a transport device.

FIG. 22 shows the support table embodiment of FIG. 21 where the depression 481 is used to receive a transport device affixed to the electrophoresis gel 500. The transport device includes a support rod 536 affixed to the electrophoresis gel 500 in some manner. The support rod 536 is received in the depression 481.

Also shown in the figure are optional magnets 606, which when used in conjunction with ferromagnetic regions 610 permanently or removably affixed below the transparent plate 415, may serve to provide a retaining force on the electrophoresis gel 500.

In another optional feature, the transparent plate 415 may include one or more rough textured regions 604 that may increase a coefficient of friction between the transparent plate 415 and the electrophoresis gel 500. A textured region 604 may include grit particles adhered to the transparent plate 415. Alternatively, a rough texture region 604 may be a sandpaper having a transparent or translucent base material onto which a grit is bonded, with the material base being affixed to the transparent plate 415. In another alternative, the textured region 604 may be merely a roughening of the surface, such as through glass beading, sandblasting, etching, scoring, etc.

FIGS. 23A–23E show detail and operation of the spot cutter head 454. The spot cutter head 454 includes a punch block 803 to which is attached a hollow punch 807, a plunger 811 that may be moved within the punch block 803 and the hollow punch 807, a punch block drive mechanism 814 that may vertically actuate the punch block 803, and a plunger drive mechanism 818 that may vertically actuate the plunger 811. The punch block drive mechanism 814 and the plunger drive mechanism 818 may be various types of drive mechanisms or actuators such as, for example, a solenoid, a pneumatic actuator, a hydraulic actuator, a worm gear drive, a crank wheel, etc.

FIGS. 23A–23E also show a fluid inlet port 813. The fluid inlet port 813 admits a fluid into the punch block 803 and hollow punch 807. The fluid may be, for example, water or pure water. In addition, there may exist a clearance between the plunger 811 and an inner surface of the hollow punch 807. The fluid may therefore be introduced into the hollow punch 807 and may be expelled from the hollow punch 807, even when the plunger 811 is fully extended.

In FIG. 23B, the punch block 803 is in a pre-punch position. The punch block 803 has been partially extended and the plunger 811 has been fully extended within the punch block 803. Therefore the plunger tip 812 extends beyond the hollow punch 807.

In FIG. 23C, the spot cutter head 454 is in a punch position wherein the punch block 803 has been fully extended, whereby the hollow punch 807 contacts the support table 404. Therefore, the hollow punch 807 passes through the electrophoresis gel 500.

In FIG. 23D, the spot cutter head 454 is in a transfer mode wherein the plunger 811 has been retracted. In addition, the punch block 803 has been fully retracted. In the transfer mode, the spot cutter head 454 may be moved, such as over the sample well 409.

Due to the presence of the fluid, retraction of the plunger 811 (see FIGS. 23C and 23D) may create a lowered fluid pressure within the punch block 803 and in the hollow punch 807, helping to retain the excised electrophoresis gel portion 888. The fluid may aid in maintaining a seal between the hollow punch 807 and the excised electrophoresis gel portion 888.

In FIG. 23E, the spot cutter mechanism 454 is in a release mode. The punch block 803 has been partially lowered over a deposit well 824 of the sample well 409 and the plunger 811 has been fully extended. The excised electrophoresis gel portion 888 is therefore expelled from the hollow punch 807.

In the release mode, the plunger tip 812 may extend beyond the hollow punch 807. Optionally, however, the plunger tip 812 could be flush with the tip of the hollow punch 807 or could be slightly recessed within the tip. In any of the above configurations, the plunger 811 must be extended far enough to expel the excised electrophoresis gel portion 888. The expulsion process may be aided by release or pressurization of the fluid admitted through the fluid inlet port 813.

After the operation of FIG. 23E, the whole process may be repeated, with the extension and retraction of the punch block 803 and hollow punch 807 and the extension and retraction of the plunger 811 being performed by the controller 400.

In this manner, the controller 400 may position the spot cutter mechanism 420, excise an electrophoresis gel portion, deposit the excised electrophoresis gel portion in a sample well, and record both the original position of the excised electrophoresis gel portion and the location of the sample well.

In operation, the fluid may be used as part of the cutting process. During the punch mode of FIG. 23C, the fluid may be introduced into the hollow punch 807. Preferably, the fluid does not exert a pressure on the electrophoresis gel 500 during the cutting step. During the transfer mode of FIG. 23D, the fluid may be maintained in the hollow punch 807 at a zero or negative relative pressure. This may be done in order to positively retain or not expel the excised electrophoresis gel region 888. During the release mode of FIG. 23E, the fluid may be equalized with an ambient air pressure. Alternatively, the fluid may be pressurized in order to aid in expelling the excised electrophoresis gel region 888. In addition, a quantity of fluid may be passed through the hollow punch 807 in order to clean it and remove the excised electrophoresis gel region 888 or to remove any sample residue. This cleaning mode may be performed, for example, over the rinse well 413 (see FIG. 14). The hollow punch 807 may optionally or alternatively be immersed in the rinse well 413.

It will be appreciated that the methods and structures of the present invention can be incorporated in the form of a variety of embodiments, only a few of which are described herein. It will be apparent to the artisan that other embodiments exist that do not depart from the spirit of the invention. Thus, the described embodiments are illustrative and should not be construed as restrictive.

What is claimed is:

1. A spot cutter for cutting spots from a loose electrophoresis gel, comprising:
    a support table including a working region capable of receiving and supporting said electrophoresis gel when said electrophoresis gel is laid loose in the absence of any attached backing material onto said working region;
    an image detector capable of imaging said electrophoresis gel when said electrophoresis gel is in position on said support table;
    a means for laying onto said working regions said electrophoresis gel loose in the absence of any attached backing material;
    a spot cutter head including a hollow punch that is capable of moving downward into contact with said support table, thereby passing through said electrophoresis gel, with said hollow punch cutting out an electrophoresis gel region substantially equal in size to an inner dimension of said hollow punch;
    a positioning mechanism for positioning said spot cutter head relative to said support table, said spot cutter head being affixed to and movable by said positioning mechanism; and
    a controller communicating with said image detector and receiving an electrophoresis gel image, positioning said positioning mechanism, and activating said spot cutter head.

2. The spot cutter of claim 1, wherein said support table further comprises a transparent plate within said working region.

3. The spot cutter of claim 2, wherein said support table further includes at least one ferromagnetic region disposed under said transparent plate.

4. The spot cutter of claim 2, wherein said support table further includes at least one depression adjacent to said transparent plate, with said at least one depression being adapted to receive an electrophoresis gel clamp affixed to said electrophoresis gel when said electrophoresis gel is in position on said support table.

5. The spot cutter of claim 1, wherein said transparent plate comprises a glass plate and said glass plate includes at least one roughened surface region, said at least one roughened surface region holding said electrophoresis gel in position on said glass plate.

6. The spot cutter of claim 1, wherein said support table further includes a rinse well capable of containing a rinse fluid, wherein a tip of said hollow punch may be immersed in said rinse well and said rinse fluid.

7. The spot cutter of claim 1, wherein said support table further includes a rinse well capable of containing a rinse fluid, wherein a fluid expelled from said spot cutter head is retained in said rinse well.

8. The spot cutter of claim 1, wherein said support table further includes at least one sample well where an excised electrophoresis gel portion is deposited.

9. The spot cutter of claim 8, wherein said controller stores coordinates of said sample well containing said excised electrophoresis gel portion.

10. The spot cutter of claim 9, wherein said at least one pivoting plate further includes a projection that extends at an angle from said at least one pivoting plate, and wherein when said at least one pivoting plate is resting on said electrophoresis gel said projection is depressed in order to pivot said at least one pivoting plate up off of said electrophoresis gel.

11. The spot cutter of claim 1, wherein said support table further includes at least one pivoting plate capable of being pivoted up and away from said electrophoresis gel when said electrophoresis gel is in position on said support table and is further capable of being pivoted down and onto said electrophoresis gel in order to hold said electrophoresis gel through a mass of said at least one pivoting plate.

12. The spot cutter of claim 1, wherein said support table is illuminated from a side opposite said image detector.

13. The spot cutter of claim 1, wherein said controller receives said electrophoresis gel image and determines spot locations in said electrophoresis gel image, with said controller excising electrophoresis gel portions that contain said spot locations.

14. The spot cutter of claim 1, wherein said image detector comprises a camera.

15. The spot cutter of claim 1, wherein said image detector comprises a digital camera.

16. The spot cutter of claim 1, wherein said image detector comprises a charge-coupled device.

17. The spot cutter of claim 1, wherein said positioning mechanism further comprises:
   a first robotic arm segment rotatably attached to a support structure, with said first robotic arm segment being rotated about a substantially vertical axis by a rotation mechanism; and
   a second robotic arm segment pivotally attached to said first robotic arm and being pivoted in a substantially horizontal plane by a second pivot drive mechanism, with said spot cutter head being attached to said second robotic arm segment;
   wherein said rotation mechanism and said second pivot drive mechanism are directed by said controller; and
   wherein said positioning mechanism enables said spot cutter head to be positioned at any location over said working region.

18. The spot cutter of claim 17, wherein said rotation mechanism and said second pivot drive mechanism are selected from the group consisting of a pneumatic actuator, a hydraulic actuator, and an electric stepper motor, an electric servo motor, and combinations thereof.

19. The spot cutter of claim 17, wherein said support structure is said support table.

20. The spot cutter of claim 1, wherein said positioning mechanism further comprises:
   a first robotic arm segment pivotally and rotatably attached to a support structure, with said first robotic arm segment being pivoted by a first pivot drive mechanism in a substantially vertical plane and rotated about a substantially vertical axis by a rotation mechanism; and
   a second robotic arm segment pivotally attached to said first robotic arm and being pivoted in a substantially vertical plane by a second pivot drive mechanism, with said spot cutter head being pivotally attached to said second robotic arm segment and pivoted by a spot cutter head pivot drive mechanism;
   wherein said first pivot drive mechanism, said rotation mechanism, said second pivot drive mechanism, and said spot cutter head pivot drive mechanism are directed by said controller; and
   wherein said positioning mechanism enables said spot cutter head to be positioned at any location over said electrophoresis gel.

21. The spot cutter of claim 20, wherein said support structure is said support table.

22. A The spot cutter of claim 20, wherein said first pivot drive mechanism, said rotation mechanism, said second pivot drive mechanism, and said spot cutter head pivot drive mechanism are selected from the group consisting of a pneumatic actuator, a hydraulic actuator; and an electric stepper motor, an electric servo motor, and combinations thereof.

23. The spot cutter of claim 1, wherein said positioning mechanism further comprises:
   a rail affixed to said support table; and
   an arm movable on said rail by a first drive mechanism, with said spot cutter head being movable on said arm by a second drive mechanism, with said arm being substantially orthogonal to said rail.

24. The spot cutter of claim 23, wherein said first drive mechanism and said second drive mechanism are selected from the group consisting of a pneumatic actuator, a hydraulic actuator, and an electric stepper motor, an electric servo motor, and combinations thereof.

25. The spot cutter of claim 1, wherein said spot cutter head further includes a punch block and said hollow punch is formed on said punch block.

26. The spot cutter of claim 1, wherein said punch block is hydraulically extended and retracted.

27. The spot cutter of claim 1, wherein said punch block is pneumatically extended and retracted.

28. The spot cutter of claim 1, wherein said spot cutter mechanism further includes a plunger inside said hollow punch, with said plunger being capable of being retracted within said hollow punch by a plunger drive mechanism during excision and further capable of being extended by said plunger drive mechanism so that a tip of said plunger approaches a tip of said hollow punch.

29. The spot cutter of claim 1, wherein said spot cutter mechanism further includes a plunger inside said hollow punch, with said plunger being capable of being retracted within said hollow punch by a plunger drive mechanism during excision and further capable of being extended by said plunger drive mechanism so that a tip of said plunger is substantially flush with a tip of said hollow punch.

30. The spot cutter of claim 1, wherein said spot cutter mechanism further includes a plunger inside said hollow punch, with said plunger being capable of being retracted within said hollow punch by a plunger drive mechanism during excision and further capable of being extended by said plunger drive mechanism so that a tip of said plunger extends beyond a tip of said hollow punch.

31. The spot cutter of claim 1, wherein said plunger drive mechanism is a hydraulic actuator.

32. The spot cutter of claim 1, wherein said plunger drive mechanism is a pneumatic actuator.

33. The spot cutter of claim 1, wherein said plunger drive mechanism is a worm gear drive.

34. The spot cutter of claim 1, wherein said plunger drive mechanism is a solenoid.

35. The spot cutter of claim 1, wherein said spot cutter head further comprises:
a fluid inlet port located on said punch block and capable of admitting a fluid into said punch block and said hollow punch; and
a clearance between said plunger and an inner surface of said hollow punch, said clearance being sufficient for a fluid flow.

36. A spot cutter for cutting spots from an electrophoresis gel, comprising:
a support table including a working region capable of receiving and supporting said electrophoresis gel when said electrophoresis gel is laid onto said working region;
an image detector capable of imaging said electrophoresis gel when said electrophoresis gel is in position on said support table;
a spot cutter head including a hollow punch that is capable of moving downward into contact with said support table, thereby passing through said electrophoresis gel, with said hollow punch cutting out an electrophoresis gel region substantially equal in size to an inner dimension of said hollow punch;
a positioning mechanism for positioning said spot cutter head relative to said support table, said spot cutter head being affixed to and movable by said positioning mechanism, said positioning mechanism having:
a first robotic arm segment rotatably attached to a support structure, with said first robotic arm segment being rotated about a substantially vertical axis by a rotation mechanism;
a second robotic arm segment pivotally attached to said first robotic arm and being pivoted in a substantially horizontal plane by a second pivot drive mechanism, with said spot cutter head being attached to said second robotic arm segment;
wherein said rotation mechanism and said second pivot drive mechanism are directed by said controller, and said positioning mechanism enables said spot cutter head to be positioned at any location over said working region; and
a controller communicating with said image detector and receiving an electrophoresis gel image, positioning said positioning mechanism, and activating said spot cutter head.

37. The spot cutter of claim 36, wherein said rotation mechanism and said second pivot drive mechanism are selected from the group consisting of a pneumatic actuator, a hydraulic actuator, and an electric stepper motor, an electric servo motor, and combinations thereof.

38. The spot cutter of claim 36, wherein said support structure is said support table.

39. A spot cutter for cutting spots from an electrophoresis gel having a limited spatial stability, comprising:
a support table including a working region capable of receiving and supporting said electrophoresis gel when said electrophoresis gel is laid loose onto said working region;
an image detector capable of imaging said electrophoresis gel when said electrophoresis gel is in position on said support table;
a spot cutter head including a hollow punch that is capable of moving downward into contact with said support table, thereby passing through said electrophoresis gel, with said hollow punch cutting out an electrophoresis gel region substantially equal in size to an inner dimension of said hollow punch;
a positioning mechanism for positioning said spot cutter head relative to said support table, said spot cutter head being affixed to and movable by said positioning mechanism, the positioning mechanism having:
a first robotic arm segment pivotally and rotatably attached to a support structure, with said first robotic arm segment being pivoted by a first pivot drive mechanism in a substantially vertical plane and rotated about a substantially vertical axis by a rotation mechanism; and
a second robotic arm segment pivotally attached to said first robotic arm and being pivoted in a substantially vertical plane by a second pivot drive mechanism, with said spot cutter head being pivotally attached to said second robotic arm segment and pivoted by a spot cutter head pivot drive mechanism;
wherein said first pivot drive mechanism, said rotation mechanism, said second pivot drive mechanism, and said spot cutter head pivot drive mechanism are directed by said controller, and said positioning mechanism enables said spot cutter head to be positioned at any location over said electrophoresis gel; and
a controller communicating with said image detector and receiving an electrophoresis gel image, positioning said positioning mechanism, and activating said spot cutter head.

40. The spot cutter of claim 39, wherein said support structure is said support table.

41. The spot cutter of claim 39, wherein said first pivot drive mechanism, said rotation mechanism, said second pivot drive mechanism, and said spot cutter head pivot drive mechanism are selected from the group consisting of a pneumatic actuator, a hydraulic actuator, and an electric stepper motor, an electric servo motor, and combinations thereof.

* * * * *